(12) United States Patent
Zech et al.

(10) Patent No.: US 8,466,210 B2
(45) Date of Patent: Jun. 18, 2013

(54) DENTAL COMPOSITION CONTAINING A SURFACTANT AND AN F-CONTAINING COMPOUND, PROCESS OF PRODUCTION AND USE THEREOF

(75) Inventors: Joachim W. Zech, Kaufering (DE); Peter U. Osswald, Tuerkheim (DE); Henning Hoffmann, Windach (DE); Andreas R. Maurer, Langenneufnach (DE); Peter Bissinger, Diessen (DE); Klaus Hintzer, Kastl (DE)

(73) Assignee: 3M Innovative Properties Company, St. Paul, MN (US)

(*) Notice: Subject to any disclaimer, the term of this patent is extended or adjusted under 35 U.S.C. 154(b) by 348 days.

(21) Appl. No.: 12/747,927

(22) PCT Filed: Dec. 17, 2008

(86) PCT No.: PCT/US2008/087087
§ 371 (c)(1),
(2), (4) Date: Jun. 14, 2010

(87) PCT Pub. No.: WO2009/079534
PCT Pub. Date: Jun. 25, 2009

(65) Prior Publication Data
US 2010/0292362 A1   Nov. 18, 2010

(30) Foreign Application Priority Data
Dec. 18, 2007  (EP) .................................. 07123485
Jul. 14, 2008  (EP) .................................. 08160310

(51) Int. Cl.
*A61K 6/10* (2006.01)
*C08L 83/04* (2006.01)
*C08G 77/50* (2006.01)
*D21H 19/32* (2006.01)

(52) U.S. Cl.
USPC ........... 523/109; 522/148; 524/860; 524/861; 524/862

(58) Field of Classification Search
USPC ........... 523/109; 522/148; 428/447; 524/860, 524/861, 862
See application file for complete search history.

(56) References Cited

U.S. PATENT DOCUMENTS 3,242,218 A   3/1966  Milller
3,715,334 A   2/1973  Karstedt
3,775,352 A   11/1973 Leonard, Jr.
(Continued)

FOREIGN PATENT DOCUMENTS

DE   3721784   1/1988
DE   4010281   10/1990
(Continued)

OTHER PUBLICATIONS

Kugel et al., "Investigation of a New Approach to Measuring Contact Angels for Hydrophilic Impression Materials," *Journal of Prosthodontics*, vol. 16, No. 2, Mar.-Apr. 2007, pp. 84-92.

(Continued)

*Primary Examiner* — Michael Pepitone
*Assistant Examiner* — Jessica Roswell
(74) *Attorney, Agent, or Firm* — Julie Lapos-Kuchar

(57) ABSTRACT

The present invention relates to a curable dental composition comprising a surfactant and an F-containing compound. The dental composition can be used e.g. as impression material and/or for the production of crown and bridges.

15 Claims, 1 Drawing Sheet

U.S. PATENT DOCUMENTS

| | | | |
|---|---|---|---|
| 3,814,730 | A | 6/1974 | Karstedt |
| 3,933,880 | A | 1/1976 | Bergstrom et al. |
| 4,035,453 | A | 7/1977 | Hittmair et al. |
| 4,273,902 | A | 6/1981 | Tomioka et al. |
| 4,657,959 | A | 4/1987 | Bryan et al. |
| 4,778,832 | A | 10/1988 | Futami et al. |
| 4,782,101 | A | 11/1988 | Waller et al. |
| 5,064,891 | A | 11/1991 | Fujiki et al. |
| 5,249,862 | A | 10/1993 | Herold et al. |
| 5,286,105 | A | 2/1994 | Herold et al. |
| 5,332,122 | A | 7/1994 | Herold et al. |
| 5,367,001 | A | 11/1994 | Itoh et al. |
| 5,464,131 | A | 11/1995 | Keller |
| 5,569,691 | A | 10/1996 | Guggenberger et al. |
| 5,597,882 | A | 1/1997 | Schiller et al. |
| 5,684,060 | A | 11/1997 | Konings et al. |
| 5,750,589 | A | 5/1998 | Zech et al. |
| 5,878,907 | A | 3/1999 | Graf |
| 5,907,002 | A | 5/1999 | Kamohara et al. |
| 5,924,600 | A | 7/1999 | Keller |
| 2,337,024 | A | 10/1999 | Abuto et al. |
| 6,135,631 | A | 10/2000 | Keller |
| 6,244,740 | B1 | 6/2001 | Wagner et al. |
| 6,291,546 | B1 | 9/2001 | Kamohara et al. |
| 6,677,393 | B1 | 1/2004 | Zech et al. |
| 6,861,457 | B2 | 3/2005 | Kamohara |
| 6,923,921 | B2 * | 8/2005 | Flynn et al. ............... 252/182.15 |
| 7,175,430 | B1 | 2/2007 | Gasser et al. |
| 2002/0193502 | A1 | 12/2002 | Hare |
| 2004/0085854 | A1 | 5/2004 | Pauser et al. |
| 2004/0124396 | A1 | 7/2004 | Flynn et al. |
| 2004/0141960 | A1 | 7/2004 | Haberlein et al. |
| 2004/0236003 | A1 | 11/2004 | Del Torto et al. |
| 2005/0089697 | A1 * | 4/2005 | Benayoun et al. ............ 428/447 |
| 2007/0015864 | A1 | 1/2007 | Hintzer et al. |
| 2007/0015937 | A1 | 1/2007 | Hintzer et al. |
| 2007/0025902 | A1 | 2/2007 | Hintzer et al. |
| 2007/0276068 | A1 | 11/2007 | Hintzer et al. |
| 2008/0319100 | A1 | 12/2008 | Bublewitz et al. |

FOREIGN PATENT DOCUMENTS

| | | |
|---|---|---|
| DE | 4137698 | 5/1993 |
| DE | 19922929 | 11/1999 |
| DE | 102006001126 | 7/2007 |
| EP | 0231420 B1 | 8/1987 |
| EP | 0232733 | 8/1987 |
| EP | 0480238 | 4/1992 |
| EP | 0613926 | 9/1994 |
| EP | 0729341 | 9/1995 |
| EP | 0730913 | 9/1996 |
| EP | 0847745 | 6/1998 |
| EP | 0863088 | 9/1998 |
| EP | 0870877 | 10/1998 |
| EP | 0885932 | 12/1998 |
| EP | 1165016 | 1/2002 |
| EP | 1290998 | 3/2003 |
| GB | 2337524 | 11/1999 |
| IE | 913497 | 4/1992 |
| JP | 02-305857 | 12/1990 |
| JP | 10-072307 | 3/1998 |
| JP | 2004/113129 | 4/2004 |
| RU | 2164400 | 3/2001 |
| WO | 00/48553 | 8/2000 |
| WO | 2004/058196 | 7/2004 |
| WO | 2004/060964 | 7/2004 |
| WO | 2004/098542 | 11/2004 |
| WO | 2007/001869 | 1/2007 |
| WO | 2007/080071 | 7/2007 |
| WO | 2007/140091 | 12/2007 |

OTHER PUBLICATIONS

Schott, "Hydrophile-Lipophile Balance and Cloud Points of Nonionic Surfactants", *J. Pharm. Science*, vol. 58, No. 12, Dec. 1969, pp. 1442-1448.

DIN EN ISO 4823, Dentistry—Elastomeric impression materials, Aug. 2001, pp. 1-36.

DIN 53018-1, Viscometry; measurement of the dynamic viscosity of Newtonian fluids by means of rotation viscometers; fundamentals, Mar. 1976, pp. 2-6.

DIN 53504, Testing of rubber; determination of tensile strength at break, tensile stress at yield, elongation at break and stress values in a tensile test, pp. May 1974, 1-7.

DIN 53 505.

International Search Report for PCT/US2008/087087, 3 pages.
International Written Opinion for PCT/US2008/087087, 6 pages.
Extended Search Report for EP 071234850, 6 pages.

* cited by examiner

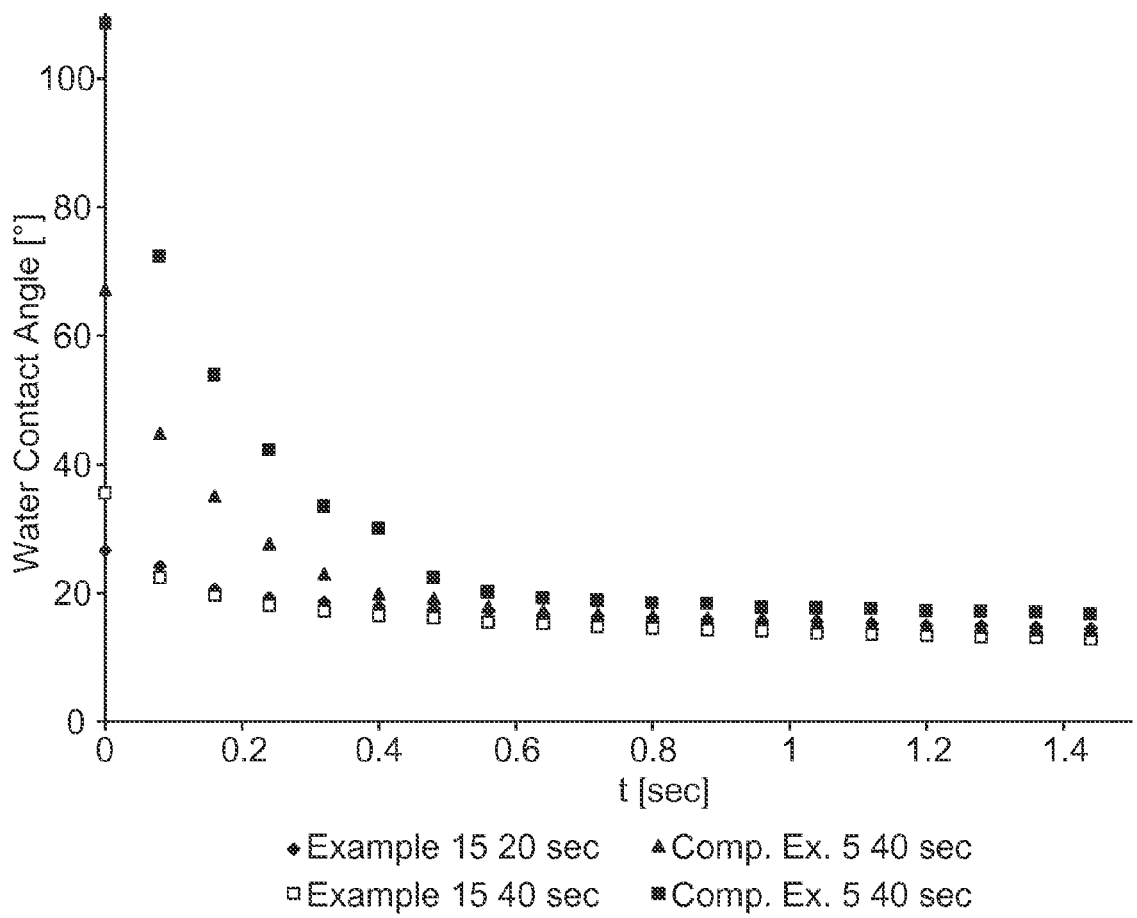

US 8,466,210 B2

DENTAL COMPOSITION CONTAINING A SURFACTANT AND AN F-CONTAINING COMPOUND, PROCESS OF PRODUCTION AND USE THEREOF

CROSS-REFERENCE TO RELATED APPLICATIONS

This application claims priority to European Patent Application No. 07123485.0, filed Dec. 18, 2007, and European Patent Application No. 08160310.2, filed Jul. 14, 2008.

FIELD OF THE INVENTION

The present invention relates to a curable dental composition comprising a surfactant and an F-containing compound. The dental composition can be used e.g. as impression material and/or for the production of crown and bridges.

BACKGROUND ART

Dental impression materials are well known in the art and have been applied for a long time. Such materials typically possess a variety of properties including a quick setting behavior, good dimensional stability and sufficient storage stability. Generally, the materials are provided in two components to be mixed prior to use and cure by a crosslinking-reaction.

One widely used class of impression materials is based on addition- or condensation crosslinking-reactions of polyorganosiloxane containing components.

Dental impression materials containing polyorganosiloxane components are typically hydrophobic in nature. In order to make these materials more hydrophilic, the incorporation of surfactants has been proposed. Measuring the contact angle of a water drop on the surface of the mixed composition is an appropriate method to find out to which extent the composition has a hydrophilic or hydrophobic behavior.

U.S. Pat. No. 5,064,891 describes an addition curable silicon composition comprising a silicone surfactant. The water contact angle measurement has been conducted on the cured material. The water contact angles measured 3 min (minutes) after the water drop has been applied on the surface of the composition was 60° and 65°, respectively.

EP 0 729 341 A1 (corresponding to U.S. Pat. No. 5,750, 589) discloses the use of a polyethercarbosilane for the hydrophilization of the impression material. The water contact angle measurement has been performed 30 min after curing of the material and values of 42° have been measured.

U.S. Pat. No. 4,657,959 contains examples of compositions containing amphoteric and ionic surfactants. With regard to non-ionic fluor-containing surfactants, perfluorinated groups are attached to a polyether moiety via a polyvalent hydrocarbonyl linking group (e.g. —$C_2H_4$— or —$SO_2NR$— group).

Addition-curing silicone impression materials formulated with a combination of a non-ionic surfactant and a methylphenylpolysiloxane are known from U.S. Pat. No. 5,907, 002. The non-ionic surfactant according to this document can possess apart from a hydrophilic group a hydrophobic group which can be either an alkyl or a fluorocarbon group. Water contact angle between 28 and 60 degree have been achieved by these formulations in the cured state.

EP 1 290 998 A1 (corresponding to U.S. Pat. No. 6,861,457 B2) describes addition-cured silicone impression material compositions, which contain an organopolysiloxane with at least two aliphatic hydrocarbon chains, a polyether with a minimum of one alkyl chain, an inorganic filling material, as well as a non-ionic nonfluorinated surfactant and/or a polyether modified silicon oil. Water contact angle measurements in the cured state were in the range of 56 to 65 degree, 1 second after setting of the drop.

EP 0 613 926 A1 (corresponding to U.S. Pat. No. 5,569, 691) discloses condensation-cured polyether impression materials, which contain at least one hydrophilic agent of the group of hydrophilic silicone oils, polyethylene glycol substituted fluorinated hydrocarbons, block copolymers of ethylenoxide and propylenoxide, fatty alcohol derivatives, alkylphenyl derivatives, fatty amines, amino oxide, fatty acid glycol or glycerine derivatives, fatty acids and fatty acid monoesters. The water contact angle measurement was performed 30 minutes after setting of the impression material and water contact angles in the range of 18 to 65 degree were found.

The use of mixtures of non-ionic surfactants to improve the wettability of the cured silicone impression material is described in US 2004/0236003 A1. Herein the non-ionic surfactants applied in the dental impression material are ethoxylated linear or branched hydrocarbon alcohols and/or acids.

In the above-mentioned patent documents the water contact angles have been exclusively determined on the cured rubber materials and, thus, the introduction of surfactants aimed mainly to improve the hydrophilicity of the set materials.

WO 2007/080071 A2 describes addition-cured dental impression materials based on silicones which provided hydrophilicity in the non-cured pasty state. By application of mixtures of fluorinated surfactants and silicone surfactants water contact angles of the pasty material below 10° were obtained 40 s (seconds) after mixing of the base and catalyst paste and 3 s after setting of the drop on the surface. The non-ionic fluorinated surfactants described contain at least one partly or per-fluorinated hydrocarbon rest, which is connected via an oxygen atom, an amino or a keto group, carboxylic ester group, a phosphoric acid ester and/or amide with an (poly)alkylenoxide radical, an carbohydrate radical, an aliphatic polyhydroxy radical or a nitrogen-containing heterocyclic compound or is at least a per- or partly fluorinated rest which comprise at least one amino-oxide rest.

The fluorinated surfactants taught in WO 2007/080071 however may not be very suitable for use in dental applications. Further it was found that generally the surfactants disclosed in this reference have an adverse impact on other desirable properties of the dental composition such as storage stability of the composition. Furthermore, it was found that the fluorinated surfactants of this PCT reference typically leach out of the composition both in its cured as well as uncured state, which may lead to a less than desired accuracy of the impression and to problems of reproducibility of the impression.

SUMMARY OF THE INVENTION

It would now be desirable to provide a further curable compositions for making impressions that can be manufactured and provided in an easy and convenient way, is easy to handle and/or is cost effective. It may also be desirable to find a curable composition, in particular an organopolysiloxane based curable composition that has good to excellent hydrophilic characteristics initially in its uncured state as well as later in its cured state. It may also be desirable to find F-containing compounds that have minimal or no leaching from the composition in its cured and/or uncured state. It would also be beneficial if the curable composition shows an improved flowing behaviour.

In one aspect, the present invention provides a curable dental composition comprising
a. a curable organopolysiloxane polymer as component (A),
b. a crosslinker compound capable of crosslinking said organopolysiloxane polymer as component (B),
c. a catalyst capable of catalyzing a crosslinking reaction or component (A) and component (B) as component (C),
d. a surfactant as component (D),
e. a F-containing compound as component (E), wherein the F-containing compound has the following formula:

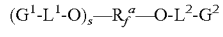

wherein:
$G^1$ and $G^2$ each independently represents a non-ionic end group that is free of polyoxyalkylene groups or contains polyoxyalkylene such that the total amount thereof in the F-containing compound is not more than 10% by weight based on the molecular weight of the F-containing compound;
$L^1$ and $L^2$ each independently represents an aliphatic (e.g. C1-C9 or C2-C6) hydrocarbon group or a partially or fully fluorinated aliphatic (e.g. C1-C9 or C2-C6) hydrocarbon group;
$R_f^a$ represents a mono-valent or divalent partially or fully fluorinated aliphatic (e.g. C1-C9 or C2-C6) group or a partially or fully fluorinated aliphatic (e.g. C1-C9 or C2-C6) group interrupted by one or more oxygen atoms;
wherein s represents 0 or 1;
with the proviso that at least one of the following conditions is fulfilled:
(i) at least one of the moieties $L^1$-$G^1$ and $L^2$-$G^2$ is partially or fully fluorinated or
(ii) $R_f$ is a partially or fully fluorinated aliphatic group (e.g. C1-C9 or C2-C6) interrupted by one or more oxygen atoms.

By the term "non-ionic end group is meant an end group that is free of groups that dissociate into ionic species in an aqueous medium. Examples of ionic groups include acid groups as well as salts.

In a particular embodiment $G^1$ and $G^2$ are independently selected from: —$COOR^a$, —$CONR^bR^c$, —$CH_2OH$, —$CF_2OR^a$, —$CHFOH$, —$CHFOR^a$, —$CH_2OR^a$ or —F with $R^a$ representing an aromatic or aliphatic hydrocarbon group optionally being substituted with a hydroxy or amino group or a halogen atom and $R^b$ and $R^c$ independently representing H or an aromatic or aliphatic hydrocarbon group optionally being substituted with a hydroxy or amino group or a halogen atom.

Further in a particular embodiment, $G^1$ and/or $G^2$ may include a group that is capable of participating in the crosslinking reaction between components (A) and (B). Accordingly, one embodiment, either or both end groups may be substituted with a functional group capable of reacting with either component (A) or (B).

In one particular embodiment, the present invention relates to a dental composition comprising
a. a curable silicone polymer as component (A), the silicone polymer containing at least two functional groups capable of reacting with a SiH group in the presence of a hydrosilation catalyst,
b. a crosslinker compound containing at least two SiH groups as component (B),
c. a catalyst capable of catalyzing a hydrosilation reaction as component (C),
d. a surfactant as component (D),
e. at least one F-containing compound as component (E), wherein the F-containing compound has the following formula

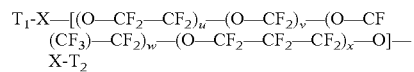

with u=0 to 8, v=0 to 8, w=0 to 8 and x=0 to 8 and u+v+w+x≧1,
wherein $T_1$ and $T_2$ can be equal or different and are independently selected from —COOR, —$CONR^bR^c$—$CH_2OH$, —$CF_2OR$, —CHFOH, —CHFOR, —$CH_2OR$ or —F with R being a linear or branched alkyl rest (C1 to C9), aryl rest (C1 to C9) or alkylaryl rest (C1 to C9) each of which may optionally be substituted with one or more substituents selected from the group consisting of hydroxyl, amino group, halogen atom, a SiH group or a group capable of reacting with SiH, Rb and Rc independently representing H or having a meaning as given for R and
wherein X is selected from —$(CF_2)_{1-6}$—, —$CF(CF_3)$— and —$CHF$—$CF_2$—.

An example of a group capable of reacting with SiH and that may be included in either or both of the end groups $T_1$ and $T_2$ includes a vinylsiloxane group such as for example a vinyldialkyl siloxane including for example $CH_2$=CH—Si$(CH_3)$—.

According to another aspect, the invention features a kit of parts comprising a base paste and a catalyst paste separated from each other before use, wherein the base paste comprises components (A) and (B) and the catalyst paste comprises component (C) or (C) and (A) and wherein component (D) and/or (E) and further optional components can be present either in the base paste or the catalyst paste or the base paste and the catalyst paste. Typically, the base paste does not comprise a catalyst.

A further aspect of the invention is directed to a method of producing a dental composition comprising the step of combining the F-containing compound with a hardenable matrix based on a curable organopolysiloxane polymer and comprising a surfactant, preferably a Si-containing surfactant.

In yet another embodiment, the invention relates to a method of using the dental composition as impression materials or for the preparation of crowns and bridges.

Moreover, the invention is also directed to a method of using the F-containing compound for enhancing the hydrophilicity of a hardenable composition based on a curable organopolysiloxane polymer and comprising a surfactant.

FIG. 1 shows the time dependency of the water contact angle of exemplified compositions.

It has been found that the addition of the F-containing compound to the formulation of an organopolysiloxane dental impression material generally has an impact on the wetting behavior (hydrophilicity) of a curable organopolysiloxane based dental composition. Typically, the wetting behavior of the dental composition with respect to hydrophilic surfaces (including human skin, mucosa, gingiva and dental tooth structure) is improved.

The F containing compounds typically have no or a very limited solubility in water. It has been found that generally the F-containing compounds used according to the invention, despite their limited solubility characteristics in water nevertheless are generally capable of improving the hydrophilicity of the curable composition, initially and/or in the cured state.

Further, the F-containing compounds typically may have a low tendency of leaching from the composition whether cured or not. Typically, the F-containing compounds have no or little adverse affects on other desired properties of the curable composition and may even improve some desired properties.

It has been found, that a dental composition comprising an F-containing compound described in the present invention, but no surfactant typically does not show an improved wetting behavior in contrast to compositions containing a typical fluorinated surfactant, such as the ethoxylated nonionic fluorosurfactant Zonyl™ FSO-100 (DuPont).

In contrast to this, a dental composition containing a certain F-containing compound in combination with a surfactant typically shows an improved wetting behavior, especially in the uncured state.

Thus, the F-containing compound may provide a synergistic effect in combination with a surfactant.

Furthermore, with respect to some embodiments, it has also been revealed that a cured dental composition containing the F-containing compound as described in the text of the invention in combination with a surfactant shows an improved storage stability, e.g. compared with a dental composition containing the F-containing compound suggested in the examples of WO 2007/080071 A2.

Moreover, with respect to some embodiments, it has also been revealed that catalyst pastes comprising F-containing compounds according to the present invention show improved storage stability. Certain embodiments are more stable than compositions containing the F-containing compound suggested in the examples of WO 2007/080071 A2.

DEFINITIONS

Within the description of the invention, the following terms are defined as follows:

The term "compound" is a chemical substance which has a particular molecular identity or is made of a mixture of such substances, e.g., polymeric substances.

The term "hydrosilation" means the addition of an organopolysiloxane compound comprising SiH-groups to a compound containing an aliphatic multiple bond (e.g., an olefinic or acetylenic unsaturation), preferably a vinyl group, —CH=$CH_2$.

By "paste" is meant a soft, viscous mass of solids dispersed in a liquid.

The term "silicone," as used herein, refers to a polymer having, for the most part, alternating silicon and oxygen atoms (i.e., a polysiloxane chemical structure) and having sufficient pendant functional groups to undergo a setting reaction in the presence of a crosslinker compound and a catalyst compound.

A "hardenable matrix" may be described as the components of a composition contributing to the formation of a network due to chemical interaction (e.g. formation of chemical bondings) between the components thereby leading to a significant change in rheological properties like viscosity.

The terms "vulcanizing, hardening, crosslinking, setting," are used interchangeable and refer to silicones that have as a common attribute the development of a crosslinked elastomer from relatively low molecular weight linear or branched polymers by means of a chemical reaction that simultaneously forms these crosslinks and effectively extends chain length at room temperature. "Room temperature vulcanizing" implies that the curing reaction can proceed at temperatures at or near 25° C. For example, the oral cavity of the mouth has an average temperature of approximately 32° C. and is therefore near room temperature. Certain "high" temperature cured materials are designed to cure only at relatively high temperatures (e.g., >50° C. or >100° C.) and are stable (i.e., the curing reaction is retarded) at room temperature for prolonged periods.

The term "crosslinked polymer," as used herein, refers to polymers that react with the functional group or groups of the polymer chains to lengthen them and connect them, e.g., to form a crosslinked network characteristic of a silicone elastomer. In contrast to a thermoplastic polymer (i.e., a polymer that softens and flows upon heating) a crosslinked polymer, after crosslinking, is characteristically incapable of further flow.

The term "working time" as used herein, refers to the time between the initiation of the setting reaction (e.g., when a vinyl-containing organopolysiloxane, a organohydropolysiloxane, and a platinum catalyst are mixed) and the time the setting reaction has proceeded to the point at which it is no longer practical to perform further physical work upon the system, e.g., reform it, for its intended purpose. When the reaction has proceeded to this later point the material is said to have reached its "gel point." The working time preferably provides enough time to mix and place the composition into its desired form. For many dental impression compositions and applications the working time under conditions of use can be greater than about 30 s (seconds), or greater than about 1 min (minute), or greater than about 2 min. Thus, the working time is typically within a range of about 30 s to about 3 min or about 1 min to about 2 min. So-called "fast-setting" compositions typically have a shorter working time, e.g. less than about 2 min or less than about 1.5 min.

The terms "set time" or "setting time" as used herein, refer to the time at which sufficient curing has occurred so that essentially the material's final cured-state properties are obtained. For a silicone impression material the set time is that time at which one may remove the material from the surface being replicated without causing permanent deformation of the silicone material. The setting time may be approximated, for example, by measuring the torque of the reacting composition on an oscillatory rheometer. When the torque value reaches a maximum value the material is said to be fully set. An arbitrary torque value which is less than the typical maximum value (e.g. 90% of the maximum value) may alternatively be used as a practical approximation of the set time. In general, shorter setting times are preferred over longer setting times. For dental impression compositions the setting time occurs at a time preferably less than about 10 minutes after initiation of the reaction. More preferably the setting time is less than the sum of about 5 minutes plus the working time. Most preferably the setting time is just longer than the desired working time.

More specifically, the setting time is the time between positioning of the spoon with the dental material in the mouth of the patient and removal of the cured material, and can also be called the mouth residence time or period. Setting times of <about 3 min mouth residence time, preferably <about 2.5 min, and particularly preferably <about 2 min are desirable properties for the dentist working with situation impression materials. For example, the one-phase impression material Imprint™ (3M ESPE) has a setting time of about 5 minutes, while a typical alginate impression material such as Palgat™ (3M ESPE) has a setting time of about 4 min.

A "dental impression" may be described as an accurate representation of part or all of a person's dentition. It forms a "negative" of a person's hard dental tissue which can then be used to make a model (physical) of the dentition. This may be used for the fabrication of dentures, crowns or other prostheses. An impression is carried out by placing a liquid material into the mouth in a customised tray. The material then sets to become an elastic solid, and when removed from the mouth retains the shape of the teeth. Common materials used for dental impressions are sodium alginate, agar, polyethers including aziridino substituted polyether materials and silicones, both condensation-cured silicones and addition-cured silicones including polyvinyl siloxanes.

The term "dental tissue" includes the hard tooth substance (enamel and dentin), the gingival region (soft dental tissue) surrounding the hard tooth substance and hard tooth substance bearing orthodontic appliances.

Surfactants, also sometimes referred to as tensides, are wetting agents that are able to lower the surface tension of a liquid, allowing easier spreading, and lower the interfacial tension between two liquids.

Surfactants are usually organic compounds that are amphiphilic, meaning they contain both hydrophobic groups ("tails") and hydrophilic groups ("heads"). Typical examples include polyethyleneglycol-substituted fatty acids.

Usually, a surfactant can be classified by the presence of formally charged groups in its head. A nonionic surfactant has no charge groups in its head. The head of an ionic surfactant carries a net charge. If the charge is negative, the surfactant is more specifically called anionic; if the charge is positive, it is called cationic. If a surfactant contains a head with two oppositely charged groups, it is termed zwitterionic.

Surfactants typically reduce the surface tension of water by adsorbing at the liquid-gas interface. They also may reduce the interfacial tension between oil and water by adsorbing at the liquid-liquid interface. Many surfactants can also assemble in the bulk solution into aggregates. Some of these aggregates are known as micelles. The concentration at which surfactants begin to form micelles is known as the critical micelle concentration (CMC).

Surfactants can also be characterized by a "Hydrophobic Lipophilic Balance" value (HLB-value). Generally, with an increasing HLB-value a substance becomes more hydrophobic and in reverse more lipophilic. The measurement of the HLB-value of a certain substance can be accomplished by determining its aqueous solubility and cloud point, using e.g. the method described by H. Schott, J. Pharm. Science, 58, 1442, (1969). E.g. according to the product description, Silwett™ L-77 (a Si-containing surfactant) is said to have an estimated HLB value in the range of 5 to 8.

The "initial water contact angle" is defined as the contact angle of a water drop at the time 0 seconds (s) of the experiment ($\Theta_{0s}$ in degrees). The starting time of the experiment is defined as the time when the cannula, which is used for setting the water drop on a surface, does not have an influence on the shape of the water drop, i.e. when the cannula was removed from the water drop as soon as possible after placing of the water drop. Thus, ideally this time corresponds to the first contact of the water drop to the surface. Furthermore, the initial contact angle can be determined for any time after mixing of base paste and catalyst paste. The term "initial" does not refer to the time after mixing. The initial contact angle can be determined from Water Contact Angle Measurement as described in more detail in the Example section below, using e.g. a goniometer DSA 10 (Krüss). A low water contact angle typically indicates a better wettability.

The term "automixer-suitable impression material" relates to a multi-component impression material which can be dispensed, for example, from a two-component disposable cartridge through a static mixer, e.g., of SulzerMixpac Company (cf. U.S. Pat. No. 5,464,131, EP 0 730 913 A1) or from film bags in dual-chamber reusable cartridges through a dynamic mixer, e.g., in the "Pentamix™", "Pentamix™ 2" and "Pentamix™ 3" devices of 3M ESPE Company (cf. U.S. Pat. No. 5,286,105 and U.S. Pat. No. 5,249,862).

By "dental composition" within the meaning of the present invention is a composition which is intended and adapted to be used in the dental field (including restorative and prosthodontic work) including the orthodontic area. In this respect, a dental composition typically does not contain hazardous substances. Commercially available products have to fulfil requirements such as those given in ISO 4823. Typically, those compositions cure or set at ambient conditions.

By a temporary or long term crown and bridge material is meant a material, which is used for the preparation of dental crowns and bridges containing hardenable monomers, including (meth)acrylates. These materials are typically used during the time period needed for making a permanent restoration. A typical time period ranges from a few days (e.g. 3 to 5) over weeks (1 to 3) to a few months (1 to 6). A long term crown and bridge material is typically used over a time period of about 6 to about 24 month.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Unless otherwise indicated, all numbers expressing quantities of ingredients, measurement of properties such as contrast ratio and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

DETAILED DESCRIPTION OF THE INVENTION

Certain embodiments of the curable dental composition can be characterized by at least one of the following features:
Consistency (according to ISO 4823): 0, 1, 2 or 3 and/or
Setting time: within about 15 min after mixing at ambient conditions (e.g. 23° C.).

That is, the curable dental composition can show a comparable low viscous behaviour (consistency 3), a medium viscosity (consistency 1 or 2) or show a putty-like behaviour (consistency 0).

Certain embodiments of the cured dental composition can be characterized by at least one of the following features:
Tensile strength (according to DIN 53504): at least about 0.2 MPa, or at least about 3.0 or at least about 4.0,
Elongation at break (according to DIN 53504): at least about 30%, or at least about 150%, or at least about 200%, Recovery from deformation (according to ISO 4823): at least about 90%, or at least about 95%, or at least about 98%, Shore A hardness (according to ISO 4823; 24 h): at least about 20 or at least about 40.

The dental composition can also be characterized by its water contact angle.

Certain embodiments of the composition have a water contact angle of less than about 20° or less than about 13° at a water drop age of 10 s, 60 s after mixing of the components (e.g. determined according to the method described in the Example section below).

Certain embodiments of the composition have alternatively or in addition to the above water contact angle an initial water contact angle of less than about 80°, 40 s after mixing of the components (e.g. determined according to the method described in the Example section below).

The dental composition according to the present invention includes an organopolysiloxane polymer, sometimes also referred to as silicone polymer in this application, as component (A), a crosslinker compound as component (B) and a suitable catalyst as component (C).

In one embodiment of the present invention, the dental composition contains as component (A) a curable silicone polymer containing at least two functional groups capable of reacting with a SiH group in the presence of a hydrosilation catalyst, Typically, the curable silicone polymer is an organopolysiloxane with at least two pendant or terminal triorganosiloxy groups in which at least one of the three organic groups is a group with an ethylenically unsaturated double bond.

Generally, the groups with an ethylenically unsaturated double bond can be located on any monomeric unit of the organopolysiloxane. It is, however, preferred, that the groups with an ethylenically unsaturated double bond are located on or at least near the terminal, monomeric units of the polymer chain of the organopolysiloxane. In another embodiment, at least two of the groups with an ethylenically unsaturated double bond are located on the terminal monomeric units of the polymer chain.

The term "monomeric units" as used throughout the present text relates to repeating structural elements in the polymer that form the polymer backbone, unless expressly stated otherwise.

Preferred organopolysiloxanes of this general structure are represented by the following formula

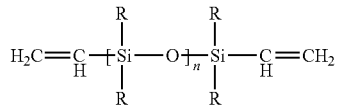

in which the radicals R, independently from each other, represent a non-substituted or substituted, monovalent hydrocarbon group with 1 to about 6 C atoms, which is preferably free from aliphatic multiple bonds and where n generally can be chosen such that the viscosity of the organopolysiloxanes lies between about 4 and about 1,000,000 mPas or between about 6 and about 500,000 or between about 10 and about 100,000 mPas. The parameter n can, e.g., be in the range of about 10 to about 10,000.

Generally, the radicals R in the above formula can represent any non-substituted or substituted, monovalent hydrocarbon group with 1 to about 6 C atoms. Non-substituted or substituted, monovalent hydrocarbon groups with 1 to about 6 C atoms can be linear or, if the number of carbon atoms exceeds 2, branched or cyclic. Generally, the radicals R can be equipped with any type of substituent or substituents provided they do not interfere with any other constituents or substituents of the composition and do not interfere with the curing reaction.

The term "interfere" as used in the context of the present text relates to any influence of such a substituent on at least one of the other substituents or constituents of the composition or the curing reaction, or both, which might be detrimental to the properties of the hardened product.

The term "detrimental" as used in the context of the present text relates to a change of properties of the precursors or the cured product that negatively affect the usefulness of the precursors or the cured product in their intended use.

In another embodiment of the invention, at least about 50% of the radicals R are methyl groups. Examples of other radicals R that can be present in the organopolysiloxanes according to the above formula are ethyl, propyl, iso-propyl, n-butyl, iso-butyl, tert-butyl, the pentyl isomers, the hexyl isomers, vinyl, allyl, propenyl, iso-propenyl, 2- and 3-n-butenyl, the pentenyl isomers, the hexenyl isomers, fluorine substituted aliphatic radicals like 3,3,3-trifluoropropyl groups, cyclopentyl or cyclohexyl groups, cyclopentenyl or cyclohexenyl groups or aromatic or heteroaromatic groups like phenyl or substituted phenyl groups. Examples for such molecules are described in U.S. Pat. No. 4,035,453, the disclosure of which, especially regarding the above mentioned molecules, their chemical constitution and their preparation, is regarded as being part of the disclosure of the present document and is included herein by reference.

The preparation of molecules according to the above-mentioned formula would generally be understood by the skilled person based upon the teachings of the prior art regarding similar molecules.

Particularly preferred are linear polydimethylsiloxanes according to the above formula having viscosities within the specified viscosity ranges and end groups comprising dimethylvinylsiloxy units and methyl groups as the radicals R.

A component (A) which can be employed according to the invention can consist of one type (A1) of organopolysiloxane. The organopolysiloxane can have a viscosity starting in the range of about 5 to about 1,000,000 mPas, or about 10 to about 500,000 mPas or about 20 to about 50,000 or about 30 to about 40,000 mPas.

It is, however, also possible that component (A) comprises two or more constituents, (A1), (A2) and so on, which can differ, e.g., in the chemical composition of their backbone, or their molecular weight, or their substituents or their viscosity, or any other differentiating feature or two or more of the above mentioned features.

In one embodiment of the invention the difference in viscosities of different constituents of component (A) can be higher than a factor of 2, e.g., higher than a factor of about 5, higher than a factor of about 10, higher than a factor of about 20, higher than a factor of about 30, higher than a factor of about 40, higher than a factor of about 50, higher than a factor of about 60, higher than a factor of about 70, higher than a factor of about 80, higher than a factor of about 90 or higher than a factor of about 100. The difference in viscosities can be even higher, e.g., higher than a factor of about 200, higher than a factor of about 300, higher than a factor of about 500, higher than a factor of about 800, higher than a factor of about 1,000 or higher than a factor of about 5,000, it should, however, preferably not exceed a value higher than a factor of about 10,000. It should be kept in mind that the values mentioned above relate to a factor for the difference in viscosities, not the viscosity values themselves.

The viscosity can be measured using a Haake Rotovisco RV20 device (spindle MV, measuring cup NV). The viscosity is typically measured at 23° C. After activation and rectification of the system, spindle MV is installed. Then the material to be measured is filled into the measuring cup NV. Without undue delay, the spindle is lowered into the measuring cup NV. The spindle should be covered by a layer of the material of a maximum thickness of 1 mm. The material to be measured is tempered for 20 min at 23° C. The measurement is started by starting the spindle to turn and the viscosity values (mPas) are recorded starting 20 s after the start of measurement. Care must be exercised to ensure that the measuring cup NV does not rotate or move at any time. A value for the viscosity is obtained in mPas. The above mentioned method of measurement corresponds to DIN 53018-1.

If component (A) contains constituents of different viscosities, the ratio of the amount of constituent with the lowest viscosity to the amount of constituent with the highest viscosity can be chosen relatively freely, depending on the desired properties of the precursors and the cured resin. It can, however, be advantageous when the ratio of the amount of constituent with the lowest viscosity to the amount of constituent with the highest viscosity is within a range of from about 1:20 to about 20:1, especially about 1:10 to about 10:1 or about 1:5 to about 5:1. Good results can e.g. be obtained with ratios of from about 1:3 to about 3:1 or about 1:2 to about 2:1. It can furthermore be adequate in some cases, when the amount of constituent with the highest viscosity is about equal to or higher than the amount of constituent with the lowest viscosity, resulting in a value of from about 0.9:1 to about 3:1 for the ratio of the amount of constituent with the highest viscosity to the amount of constituent with the lowest viscosity. All of the ratios are based on the weight of the constituents.

In certain embodiment of the invention, the dental composition can comprise as part of component (A) multifunctional (including tri- or quadri-functional) ethylenically unsaturated compounds. These compounds might contribute to improve the tensile strength of the cured composition.

These compounds include the silane compounds described e.g. in WO 2004/098542 (component (H)) and the QM resins (quadric-functional unsaturated siloxane) described e.g. in US 2002/0193502, especially those mentioned in sections [0024] to [0026]. The disclosure of these documents with respect to the silane compounds and the QM resins is expressly mentioned and herewith incorporated by reference and regarded as part of the disclosure of the invention.

The component (H) described in WO 2004/098542 contains at least one silane compound with at least 2 ethylenically unsaturated groups. Preferred silane compounds follow the general formula $Si(R^1)_n(R^2)_{4-n}$, wherein $R^1$ is a linear, branched or cyclic monovalent ethylenically unsaturated substituent which can undergo an addition reaction with SiH-groups, having from 2 to 12 carbon atoms, $R^2$ is a monovalent radical without groups that can undergo an addition reaction with SiH-groups or have a detrimental influence on such a reaction with 1 to 12 carbon atoms and n is 2, 3 or 4. Especially preferred radicals $R^1$ include vinyl, allyl and propargyl, especially preferred radicals $R^2$ include linear or branched C1-C12 alkyl groups.

In the dental composition according to the above embodiment using a curable silicone polymer containing at least two functional groups capable of reacting with a SiH group as component (A), the composition further comprises as component (B) or part of component (B) a crosslinker compound containing at least two or three SiH groups.

By definition, an organohydrogenpolysiloxane according to the present text does not belong to the group of organopolysiloxanes used as component (A) or part of component (A) as described in the context of this embodiment.

An organohydrogenpolysiloxane for use as component (B) typically contains from about 0.01 to about 1.7 wt.-% silicon-bonded hydrogen or from about 1.0 to 9.0 mmol SiH/g. The silicon valencies which are not saturated with hydrogen or oxygen atoms are typically saturated with monovalent hydrocarbon radicals R free from ethylenically unsaturated bonds.

The hydrocarbon radicals R, which may be selected independently from each other, represent a linear or branched or cyclic, non-substituted or substituted, aliphatic or aromatic monovalent hydrocarbon groups with 1 to 12 C atoms without ethylenically unsaturated bonds. In a preferred embodiment of the invention, at least about 50%, preferably about 100%, of the hydrocarbon radicals R that are bonded to silicon atoms are methyl radicals.

Organohydrogenpolysiloxanes which can be suitable as component (B) include those having a viscosity of about 10 to about 1,000 mPas or from about 15 to about 550 mPas or from about 20 to about 150 mPas.

The composition of the present embodiment also contains a catalyst as component (C) or as a part of component (C) capable of catalyzing a hydrosilation reaction.

This catalyst is typically a platinum catalyst or a platinum containing catalyst, including a platinum complex which can be prepared from hexachloroplatinum acid by reduction with tetramethyldivinyldisiloxane. Such compounds are known to the skilled person. Any other compounds which catalyze or accelerate addition cross-linking of silanes with ethylenically unsaturated double bonds are also suitable. Platinum-siloxane complexes as described, e.g. in U.S. Pat. No. 3,715,334, U.S. Pat. No. 3,775,352 and U.S. Pat. No. 3,814,730 are suitable. The disclosure of these patents with regard to platinum complexes and their preparation is explicitly mentioned and expressly regarded as part of the disclosure of the present text.

The catalyst can typically be used in an amount of about 0.00005 to about 0.05 wt.-%, particularly about 0.0002 to about 0.04 wt.-%, each calculated as elemental platinum and related to the overall weight of the composition.

Components (A), (B) and (C) are constituents of the hardenable matrix of the dental composition.

In an alternative embodiment, the dental composition may employ a curable silicone polymer composition based on a condensation curing of a condensation curable silicone polymer. Condensation curable organopolysiloxanes have been described in for example DE 41 37 698. Examples of dental compositions based on a condensation curable silicone polymer include as components (A) and (B) of the curable composition a polydialkylsiloxane having at least two hydroxy groups and a silane compound having two or more hydrolysable groups such as for example alkoxy groups. As a curing catalyst, tin or titanium compounds may be used.

An example of a suitable polysiloxane having two or more hydroxy groups includes polydialkylsiloxanes, for example polydimethylsiloxane, that are terminated with a hydroxy group at both opposite ends of the polymer chain. Generally, the hydroxyl terminated polydialkylsiloxanes will have a weight average molecular weight of about 900 to 500,000, for example between 1500 and 150,000 g/mol.

Suitable silane compounds having two or more hydrolysable groups include in particular esters of silic acid, esters of polysilic acid and polysiloxanes having two or more alkoxy groups bound to a silicium atom. Typical examples include compounds according to the formula:

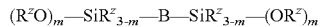

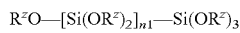

wherein in the above B represents the divalent group of formula —O—(SiR$_2$—O)$_{m2}$— with R representing an aromatic or aliphatic hydrocarbon group which may optionally be substituted and m2 represents a value of 10 to 6000, R' and R$^z$ independently represents an alkyl group or an aryl group that may be substituted, n1 represents a value of 1 to 100, m is an integer of 1 to 3 and z is 0, 1 or 2.

Suitable condensation cure catalysts include organo zinc compounds, titanates, zirconates such as for example tetraethyltitanate, tetraisopropyltitanate, tetra-n-propyltitanate, tetra-n-butyltitanate, dioctylzincdilaurate, dibutylzincdilaurate, tetra-n-butylzirconate and tetra-n-propylzirconate.

The dental composition according to the present invention includes a surfactant or surfactant mixture as component (D). Surfactants or hydrophilizing agents which can be employed can generally be chosen freely from all types of surfactants which improve the hydrophilicity of a silicone moiety containing material (especially, if curable via a hydrosilylation reaction).

Preferably, the use of the surfactant does not negatively impact the material properties or curing behaviour of the curable composition or at least not more than avoidable or tolerable.

Useful surfactants, which can improve the hydrophilicity of a silicone material according to the invention, can generally be chosen from anionic, cationic or non-ionic surfactants or mixtures of two or more of such types of surfactants.

It can be preferred, if the material according to the invention comprises a non-ionic surfactant as a hydrophilizing agent or a mixture of two or more non-ionic surfactants.

Component (D) can comprise an agent or a plurality of agents which are generally capable of increasing the hydrophilic character to a composition, for example as demonstrated by a decrease in the wetting angle of a drop of water or an aqueous solution or dispersion (e.g. a plaster suspension or the like) on the material (in its cured or uncured state) over that wetting angle achieved on the same silicon composition without component (D).

In certain embodiments, the surfactant does not contain reactive groups so that it is not incorporated into the polysiloxane network.

In certain embodiments the surfactant or at least one of the surfactants, if component (D) comprises two or more surfactants, contains a Si-containing moiety, that is, it can be referred to as a Si-containing surfactant.

Ethoxylated fatty alcohols which are e.g. described in EP 0 480 238 B1 can be used, as well.

Also preferred are the non-ionic surface-active substances which are described in U.S. Pat. No. 4,782,101, i.e. the nonylphenolethoxylates, polyethylene glycol-mono- and diesters, sorbitan esters as well as polyethylene glycol-mono- and diethers listed therein. The contents of the latter documents with regard to hydrophilizing agents and their preparation is expressly mentioned by reference and is regarded as part of the disclosure of the invention.

Suitable hydrophilizing agents can be wetting agents from the group of hydrophilic silicone oils, which are not capable of being covalently incorporated into the hardened polymer network. Suitable hydrophilizing agents are described e.g. in U.S. Pat. No. 4,657,959 and in EP 0 231 420 B1, the contents of which with regard to the hydrophilizing agents are expressly mentioned by reference and are regarded as part of the disclosure of the invention.

Useful surfactants also include polyether carbosilanes of the general formula Q-P—(OC$_n$H$_{2n}$)$_x$—OT, in which Q stands for R$_3$—Si— or

where every R in the molecule can be the same or different and stands for an aliphatic C$_1$-C$_{18}$, a cycloaliphatic C$_6$-C$_{12}$ or an aromatic C$_6$-C$_{12}$ hydrocarbon radical, which can optionally be substituted by halogen atoms, R' is a C$_1$-C$_{14}$ alkylene group, R" is R in the case of a≠0 or is R or R$_3$SiR' in the case of a=0, and a=0-2; P stands for a C$_2$-C$_{18}$ alkylene group, preferably a C$_2$-C$_{14}$ alkylene group or A-R''', where A represents a C$_2$-C$_{18}$ alkylene group and R''' a functional group from the following list: —NHC(O)—, —NHC(O)—(CH2)$_{n-1}$—, —NHC(O)C(O)—, —NHC(O)(CH2)$_v$C(O)—, —OC(O)—, —OC(O)—(CH2)$_{n-1}$—, —OC(O)C(O)—, —OC(O)(CH$_2$)$_v$C(O)—, —OCH$_2$CH(OH)CH$_2$OC(O)(CH2)$_{n-1}$—, —OCH$_2$CH(OH)CH$_2$OC(O)(CH2)$_v$C(O)— with v=1-12; T is H or stands for a C$_1$-C$_4$ alkyl radical or a C$_1$-C$_4$ acyl radical; x stands for a number from 1 to 200 and n stands for an average number from 1 to 6, preferably 1 to 4. Thus, the element —SiR"$_2$— can also comprise the substructure —Si(R)(R$_3$SiR')—.

The polyether part can be a homopolymer, but can also be a statistical, alternating or block copolymer.

Surfactants which can also be used, either alone or as a mixture of two or more thereof, can be found in U.S. Pat. No. 5,750,589 (Zech et al), col. 2, l. 47 to col. 3 l. 27 and col. 3, l. 49 to col. 4, l. 4 and col. 5, l. 7 to col. 14, l. 20.

Other surfactants which can be used, either alone or as a mixture of two or more thereof, can be found in U.S. Pat. No. 4,657,959 (Bryan et al.), col. 4, l. 46 to col. 6. l. 52 as well as in EP 0 231 420 B1 (Gribi et al.) p 4, l. 1 to p. 5, l. 16 and in the examples.

U.S. Pat. No. 5,750,589, U.S. Pat. No. 4,657,959 and EP 0 231 420 B1 are expressly described and cited herein as a source of disclosure for compounds which can be used as component (D) according to the invention. The documents and especially their disclosure with regard to hydrophilizers at the citations given above are incorporated by reference and are considered as being a part of the disclosure of the present text.

Some of the surfactants can be summarized under the following formula

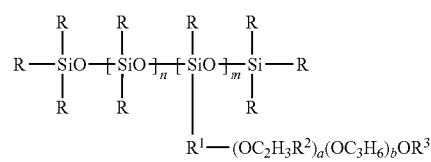

where each R is independently a monovalent hydrocarbyl radical with 1 to 22 C-atoms, R$^1$ is a divalent hydrocarbylene radical 1 to 26 C-atoms, each R$^2$ is independently hydrogen or a lower hydroxyalkyl radical, R$^3$ is hydrogen or a monovalent hydrocarbyl radical with 1 to 22 C-atoms, n and b are independently greater than or equal to zero, and m and a are independently greater than or equal to one, with the proviso that a has a sufficient value and b is small enough so that a cured composition of the invention has the desired water contact angle.

Preferably R and R³ are —CH₃, R¹ is —C₃H₆—, R² is hydrogen, n is about zero or about one, m is about one to about five, a is about five to about 20 and b is about 0.

Several of such ethoxylated surfactants are for example available from Momentive Performance Materials Inc. including "SILWET" surface active copolymers. Preferred surface active copolymers include Silwet 35, Silwet L-77, Silwet L-7600 and Silwet L-7602, Silwet L-7608 and Silwet Hydrostable 68 and Silwet Hydrostable 611. Silwet L-77 is an especially preferred ethoxylated surfactant which is believed to correspond to the above formula where R and R³ are —CH₃, R¹ is —C₃H₆—, R² is hydrogen, n is about zero or about one, m is about one or about two, a is about seven, and b is about 0. Also possible is the use of MASIL® SF19, as obtainable from Lubrizol performance products, Spartanburg, US.

Also possible is the use of polyether carbosilanes selected from the group consisting of:
Et₃Si—(CH₂)₃—O—(C₂H₄O)y-CH₃, Et=Ethyl
Et₃Si—CH₂—CH₂—O—(C₂H₄O)y-CH₃, Et=Ethyl
(Me₃Si—CH₂)₃Si—(CH₂)₃—O—(C₂H₄O)y-CH₃, Me=Methyl
Me₃Si—CH₂—SiMe₂-(CH₂)₃—O—(C₂H₄O)y-CH₃, Me=Methyl
(Me₃Si—CH₂)₂SiMe-(CH₂)₃—O—(C₂H₄O)y-CH₃, Me=Methyl
Me₃Si—(CH₂)₃—O—(C₂H₄O)y-CH₃, Me=Methyl
Me₃Si—CH₂—CH₂—O—(C₂H₄O)y-CH₃, Me=Methyl
Ph₃Si—(CH₂)₃—O—(C₂H₄O)y-CH₃, Ph=phenyl
Ph₃Si—CH₂—CH₂—O—(C₂H₄O)y-CH₃, Ph=phenyl
Cy₃Si—(CH₂)₃—O—(C₂H₄O)y-CH₃, Cy=cyclohexyl
Cy₃Si—CH₂—CH₂—O—(C₂H₄O)y-CH₃, Cy=cyclohexyl
(C₆H₁₃)₃Si—(CH₂)₃—O—(C₂H₄O)y-CH₃
(C₆H₁₃)₃Si—CH₂—CH₂—O—(C₄H₄O)y-CH₃ in which y conforms to the relation: $5 \leq y \leq 20$.

In a particular embodiment of the present invention, a mixture of a Si-containing surfactant, for example a Si-surfactant as exemplified above, and one or more non-ionic surfactants selected from alkoxylated hydrocarbon surfactants. Examples of useful non-ionic surfactants include those according to the formula:

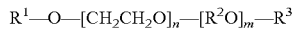

$$R^1—O—[CH_2CH_2O]_n—[R^2O]_m—R^3$$

wherein R¹ represents an aromatic or aliphatic, linear or branched hydrocarbon group having at least 8 carbon atoms, R² represents an alkylene having 3 carbon atoms, R³ represents hydrogen or a C1-C3 alkyl group, n has a value of 0 to 40, m has a value of 0 to 40 and the sum of n+m being at least 2. It will be understood that in the above formula, the units indexed by n and m may appear as blocks or they may be present in an alternating or random configuration. Examples of non-ionic surfactants according to the formula above include alkylphenol oxethylates such as ethoxylated p-isooctylphenol commercially available under the brand name TRITON™ such as for example TRITON™ X 100 wherein the number of ethoxy units is about 10 or TRITON™ X 114 wherein the number of ethoxy units is about 7 to 8. Still further examples include those in which R¹ in the above formula represents an alkyl group of 4 to 20 carbon atoms, m is 0 and R³ is hydrogen. An example thereof includes isotridecanol ethoxylated with about 8 ethoxy groups and which is commercially available as GENAPOL®X080 from Clariant GmbH. Non-ionic surfactants according to the above formula in which the hydrophilic part comprises a block-copolymer of ethoxy groups and propoxy groups may be used as well.

Such non-ionic surfactants are commercially available from Clariant GmbH under the trade designation GENAPOL® PF 40 and GENAPOL® PF 80. Further suitable non-ionic surfactants that are commercially available include Tergitol™ TMN 6, Tergitol™ TMN 10, or Tergitol™ TMN 100X. Also statistical, alternating or block copolymers of ethylene oxide and propylene oxide are suitable surfactants according to the present invention. Such non-ionic surfactants are available e.g. under the trade name Breox A, Synperonic or Pluronic.

Surfactants can be present in the composition in an amount of more than about 0.1 wt.-%, with respect to the weight of the whole composition. It can be preferred if the amount of component (D) is in a range of from about 0.1 to about 15 wt.-% or from about 0.3 to about 12 wt.-% or from about 0.5 to about 8 wt.-% or from about 0.8 to about 7 wt.-% or from about 1 to about 6 wt.-% or from about 1.2 to about 5 wt.-%. The composition of the invention is typically obtained by mixing a base paste and a catalyst paste. In this respect, the surfactant can be present in the base paste or the catalyst paste, or in the base paste and the catalyst paste. In one embodiment of the invention, the surfactant is present in the base paste only.

The F-containing compound(s) used in the composition of the present invention can be simple compounds, polymeric or oligomeric. When the F-containing compound is oligomeric of polymeric, it can be a homopolymer or copolymer. Suitable copolymeric structures include block-copolymers, alternating or statistic polymers as well as random copolymers.

The composition comprises an F-containing compound having generally a linear or branched backbone. The per- or partly fluorinated backbone of the F-containing compound is typically interrupted by one or more oxygen atoms.

Furthermore, certain embodiments of the F-containing compound can be characterized by one or more of the following features:

Chain-length of the backbone: more than about 8 atoms and less than about 100, for example not more than 50, for example less than 36 atoms (atoms counted along the longest chain in the molecule without taking into account the end groups T, G¹ and G² in the above formulas.

Containing 1 to about 10 or 2 to about 8 or 2 to about 6 ether structure elements.

Containing at least one, two, three, four, five, six, seven or eight oxygen atom(s) connecting per- or partly fluorinated elements selected from CF₃—, —CHF—, —CF₂—, CF₃—CF₂—, —CF₂—CF₂—, —CHF—CF₂—, CF₃—CHF—, CF₃—CF₂—CF₂—, —CF₂—CF₂—CF₂—, —CF(CF₃)—CF₂—, —CF(CF₃)—, —CF₃—CF₂—CF₂—CF₂—, CF₃—CF₂—CF₂—.

The terminal groups in the molecule can be a perfluor or partly fluorinated linear or branched alkyl chain (e.g. C1-C6), a fluorine atom, an alcohol, an ether functionality or an ester functionality, wherein both terminal groups can be equal or different. The preferred esters or ethers are typically based on linear or branched C1-C9 alkyl chains, C1-C9 aryl residues or C1-C9 alkylaryl residues.

The per- or partly fluorinated chain-segments of the main-chain do typically not comprise more than 5 atoms in a row.

The F-containing compound is preferably a low molecular compound with a molecular weight (Mn) equal or below about 3000 g/mol or equal or below about 2000 g/mol.

Typically, the molecular weight (Mn) is above about 200 or above about 250 or above about 300. Thus, the molecular weight of the F-containing compound is typically within a range of about 200 to about 3000 or about 250 to about 2500 or about 300 to about 2000. In a particularly preferred embodiment, the number average molecular weight is less than 3000 g/mol or not more than 1800 g/mol and the fraction of molecules have a molecular weight of 750 g/mol or less is not more than 10% by weight or not more than 5% by weight based on the total weight of F-containing compound.

The F-containing compound is typically present in the curable dental composition in an amount effective to provide either a composition having a water contact angle of less than about 20° or less than about 13° at a water drop age of 10 s ($\Theta_{10s}$), determined according to the method described below, not later than 60 s after mixing of the components and/or an initial water contact angle ($\Theta_{0s}$) of less than about 82°, not later than 40 seconds after mixing of the components.

Typically, the F-containing compound is present in the curable composition in an amount of about 0.1 to about 5 wt.-% or about 0.2 to about 4 wt.-% with respect to the whole composition.

If the composition is provided as a kit of parts comprising a base paste and a catalyst paste, the F-containing compound can be present either in the base paste or the catalyst paste or in the base paste and the catalyst paste.

If the F-containing compound is present in the base paste, it is typically present in an amount of about 0.1 to about 6 wt.-% or about 0.2 to about 5 wt.-% or about 0.3 to about 4 wt.-% with respect to the whole weight of the base paste.

If the F-containing compound is present in the catalyst paste, it is typically present in an amount of about 0.1 to about 6 wt.-% or about 0.2 to about 5 wt.-% or about 0.3 to about 4 wt.-% with respect to the whole weight of the catalyst paste.

With respect to certain embodiments, it can be desirable if the F-containing compound is present in the catalyst paste only. This may contribute to providing a storage stable composition.

According to one embodiment of the invention, the molar ratio of F-containing compound to surfactant can be in a range of about 0.05 to about 4 or about 0.08 to about 2.4 or about 0.1 to about 1.8

According to another embodiment of the invention the fluor content of the F-containing compound can be in a range of about 10 to about 90 wt.-% or about 40 to about 70 wt.-% with respect to the molecular weight (Mn) of the F-containing compound.

Specific examples of the F-containing compound include:
Rf—(O)$_t$—CHF—(CF$_2$)$_x$-T, with t=0 or 1, x=0 or 1 and Rf being a linear or branched per- or partly fluorinated alkyl rest (including C1 to C6 or C1 to C4), wherein the alkyl chain can be interrupted by O atoms, with the proviso that when t is 0, the Rf group is a linear or branched per- or partly fluorinated alkyl rest (including C1 to C6 or C1 to C4) interrupted by one or more O atoms Rf—(OCF$_2$)$_m$—O—CF$_2$-T, with m=1 to about 6 and Rf being a linear or branched per- or partly fluorinated alkyl rest (including C1 to C6 or C1 to C4), wherein the alkyl chain can be interrupted by O atoms, CF$_3$—(CF$_2$)$_2$—(OCF(CF$_3$)—CF$_2$)$_z$—O-L-T, with z=0, 1, 2, 3, 4, 5, 6, 7 or 8, L having a structure selected from —CF(CF$_3$)—, —CF$_2$—, —CF$_2$CF$_2$— and —CHFCF$_2$, Rf—(O—CF$_2$CF$_2$)$_n$—O—CF$_2$-T, with n=1, 2, 3, 4 or 5 and Rf being a linear or branched per- or partly fluorinated alkyl rest (including C1 to C6 or C1 to C4), wherein the alkyl chain can be interrupted by O atoms, an oligomeric compound obtainable by the anionic or photochemical (in the presence of oxygen) polymerization or copolymerisation of monomers selected from vinylidenfluoride, hexafluoropropylenoxide, tetrafluoroethylene, 2,2,3,3-tetrafluorooxetane, trifluoroethylene or monofluoroethylene, wherein at least one chain-end of the oligomeric compound is represented by a function T.

Specific examples include
a) homo- or copolymerization of hexafluoropropylenoxide and/or 2,2,3,3-tetrafluorooxetane and
b) homo- or copolymerization of vinylidenfluoride, hexafluoropropylenoxide, tetrafluoroethylene, 2,2,3,3-tetrafluorooxetane, trifluoroethylene and/or monofluoroethylene in the presence of oxygen.

T is typically selected from the group consisting of —COOR, —CONR$^b$R$^c$ —CH$_2$OH, —CF$_2$OR, —CHFOH, —CHFOR, —CH$_2$OR or —F with R and is a linear or branched alkyl rest (C1 to C9), aryl rest (C1 to C9) or alkylaryl rest (C1 to C9) each of which may optionally be substituted with one or more substituents selected from the group consisting of hydroxyl, amino group, halogen atom, an SiH group and a group capable of reacting with SiH, R$^b$ and R$^c$ independently representing H or having a meaning as given for R.

In particular, the esters, especially the methylesters, and the amidols (T=C(O)NH-alkyl-OH) and the respective alcohols or methylethers, prepared by chemical reduction, of the following structures can be used. Specific examples of F-containing compounds, which can be used, include those listed below:

Rf—O—CHF-T, with Rf being a linear or branched per- or partly fluorinated alkyl chain (including C1 to C6), which can be interrupted by oxygen atoms.

Specific examples according to the above formula include:
CF$_3$—O—CF$_2$—O—CF$_2$—CF$_2$—O—CHF-T
CF$_3$—(O—CF$_2$)$_2$—O—CF$_2$—CF$_2$—O—CHF-T and
CF$_3$—(O—CF$_2$)$_3$—O—CF$_2$—CF$_2$—O—CHF-T Rf—O—CHF—CF$_2$-T, with Rf being a linear or branched per- or partly fluorinated alkyl chain (including C1 to C6), which can be interrupted by oxygen atoms.
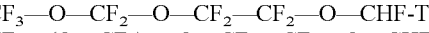
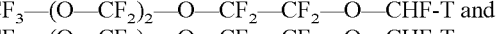
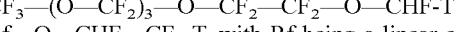

R$_f$—O—CF$_2$—CHF-T, with Rf being a linear or branched per- or partly fluorinated alkyl chain (including C1 to C6), which can be interrupted by oxygen atoms.

Specific examples according to the above formula include:
C$_3$F$_7$—O—CF$_2$—CHF-T
CF$_3$—O—CF$_2$—O—CF$_2$—CF$_2$—O—CF$_2$—CHF-T
CF$_3$—(O—CF$_2$)$_2$—O—CF$_2$—CF$_2$—O—CF$_2$—CHF-T and
CF$_3$—(O—CF$_2$)$_3$—O—CF$_2$—CF$_2$—O—CF$_2$—CHF-T Rf—O—CF$_2$—CHF—CF$_2$-T, with Rf being a linear or branched per- or partly fluorinated alkyl chain (including C1 to C6), which can be interrupted by oxygen atoms.

Specific examples according to the above formula include:
C$_3$F$_7$—O—CF$_2$—CHF—CF$_2$-T
CF$_3$—O—CF$_2$—CF$_2$—CF$_2$—O—CF$_2$—CHF—CF$_2$-T
CF$_3$—O—CF$_2$—O—CF$_2$—CF$_2$—O—CF$_2$—CHF—CF$_2$-T
CF$_3$—(O—CF$_2$)$_2$—O—CF$_2$—CF$_2$—O—CF$_2$—CHF—CF$_2$-T and
CF$_3$—(O—CF$_2$)$_3$—O—CF$_2$—CF$_2$—O—CF$_2$—CHF—CF$_2$-T R$_f$—O—CF$_2$—CF$_2$-T, with Rf being a linear or branched per- or partly fluorinated alkyl chain (including C1 to C6), which can be interrupted by oxygen atoms, n=1, 2 or 3 and m=0 or 1.

Specific examples according to the above formula include:
$CF_3—O—CF_2—CF_2$-T
$C_2F_5—O—CF_2—CF_2$-T
$C_3F_7—O—CF_2—CF_2$-T and
$C_4F_9—O—CF_2—CF_2$-T
Rf—$(O—CF_2)_u$—O—$CF_2$-T, with Rf being a linear or branched per- or partly fluorinated alkyl chain (including C1 to C6), which can be interrupted by oxygen atoms, and u=1, 2, 3, 4, 5 or 6.

Specific examples according to the above formula include:
$CF_3$—$(O—CF_2)_3$—O—$CF_2$-T and
$CF_3$—$(O—CF_2)_5$—O—$CF_2$-T
Rf—$(O—CF_2—CF_2)_k$—O—$CF_2$-T, with Rf being a linear or branched per- or partly fluorinated alkyl chain (including C1 to C6), which can be interrupted by oxygen atoms and k=1, 2, 3, 4, 5.
$C_2F_5$—$(O—CF_2—CF_2)_1$—O—$CF_2$-T
$C_3F_7$—$(O—CF_2—CF_2)_1$—O—$CF_2$-T
$C_4F_9$—$(O—CF_2—CF_2)_1$—O—$CF_2$-T
$C_2F_5$—$(O—CF_2—CF_2)_2$—O—$CF_2$-T
$CF_3$—$(O—CF_2—CF_2)_2$—O—$CF_2$-T
$C_3F_7$—$(O—CF_2—CF_2)_2$—O—$CF_2$-T and
$C_4F_9$—$(O—CF_2—CF_2)_2$—O—$CF_2$-T
Rf—O—$CF_2$-T, with Rf being a linear or branched per- or partly fluorinated alkyl chain (including C1 to C6), which can be interrupted by oxygen atoms.

Specific examples according to the above formula include:
$C_3F_7$—O—$CF_2$-T and
$CF_3$—$(CF_2)_2$—$(O—CF(CF_3)—CF_2)_z$—O—$CF(CF_3)$-T
with z=0, 1, 2, 3, 4, 5, 6, 7 or 8.

Specific examples according to the above formula include:
$CF_3$—$(CF_2)_2$—$(O—CF(CF_3)—CF_2)_2$—O—$CF(CF_3)$-T
$CF_3$—$(CF_2)_2$—$(O—CF(CF_3)—CF_2)_3$—O—$CF(CF_3)$-T
$CF_3$—$(CF_2)_2$—$(O—CF(CF_3)—CF_2)_4$—O—$CF(CF_3)$-T
$CF_3$—$(CF_2)_2$—$(O—CF(CF_3)—CF_2)_5$—O—$CF(CF_3)$-T
$CF_3$—$(CF_2)_2$—$(O—CF(CF_3)—CF_2)_z$—O—$CF(CF_3)$—$CONHCH_2CH_2OH$
$CF_3$—$(CF_2)_2$—$(O—CF(CF_3)—CF_2)_z$—O—$CF(CF_3)$—$CONHCH_2CH_2O—Si(CH_3)_2—CH=CH_2$ and
$CF_3$—CHF—O—$(CF_2)_o$-T, with o=1, 2, 3, 4, 5 or 6.

Specific examples according to the above formula include:
$CF_3$—CFH—O—$(CF_2)_3$-T
$CF_3$—CFH—O—$(CF_2)_5$-T and
$CF_3$—$CF_2$—O—$(CF_2)_o$-T, with o=1, 2, 3, 4, 5 or 6.

Specific examples according to the above formula include:
$CF_3$—$CF_2$—O—$(CF_2)_3$-T
$CF_3$—$CF_2$—O—$(CF_2)_5$-T
T-$CF_2$—O—$(CF_2—CF_2—O)_p$—$(CF_2—O)_q$—$CF_2$-T, with p/q=about 0.5 to about 3.0 and an molecular weight in the range of about 500 to about 4000 g/mol and
T-$CF_2$—$(O—CF(CF_3)—CF_2)_n$—$(O—CF_2)_m$—O—$CF_2$-T with n/m=about 20 to about 40 and a molecular weight in the range of about 650 to about 3200 g/mol.
Rf—$(O—CF_2—CF_2—CF_2)_n$—O—$CF_2$—$CF_2$-T with n=1-25 and Rf being a linear or branched per- or partly fluorinated alkyl chain (including C1 to C6), wherein the alkyl chain can be interrupted by O atoms.

In the above formulas T is selected from the group consisting of —COOR, —$CONR^bR^c$, —$CH_2OH$, —$CF_2OR$, —CHFOH, —CHFOR, —$CH_2OR$ or —F with R and being a linear or branched alkyl rest (C1 to C9), aryl rest (C1 to C9) or alkylaryl rest (C1 to C9) each of which may optionally be substituted with one or more substituents selected from the group consisting of hydroxyl, amino group, halogen atom, an SiH group and a group capable of reacting with SiH, $R^b$ and $R^c$ independently representing H or having a meaning as given for R.

Suitable fluorinated compounds for use in connection with the present invention include fluorinated polyethers that are commercially available under the tradenames FOMBLIN, GALDEN and H-Galden, Fluorolink materials or may be prepared using preparation methods described in US2007/0276068, EP 870877, WO 2004/060964, WO 2007/140091, US-A-20070015864, US-A-20070015864, US-A-20070025902 and US-A-20070015937.

In another specific embodiment of the invention, the curable dental composition comprises at least two different F-containing components. It has been found, that a mixture of different F-containing components may provide such further advantages as lowering the total amount of fluorinated compounds needed to achieve a certain desired level of hydrophilicity.

An example of a useful mixture of F-containing compounds includes a mixture of a hexafluoropropylene oxide based compound or derivative and 1H,1H-perfluor-3,6,9-trioxatridecan-1-ol. Examples of suitable hexafluoropropylene oxide (HFPO) derivatives include carboxyl ester derivatives and amidol derivatives of HFPO.

HFPO can be obtained as described in U.S. Pat. No. 3,242,218 or US 2004/0124396. The general formula of a methyl ester derivative of HFPO is $C_3F_7O[CF(CF_3)CF_2O]_nCF(CF_3)COOCH_3$ with n being 1 to 8.

According to another embodiment, the composition may contain a filler or a mixture of fillers, e.g. as component (F) or as a part of component (F), even if the presence of a filler is not mandatory. The nature of the filler is not particularly limited.

Typically filler can be used in an amount of from of at least about 5 wt.-% or at least about 20 or at least about 35 wt.-% with respect to the whole composition.

There is no particular upper limit, however, typically the amount of filler, if present at all, is used in an amount of at most about 80 wt.-% or at most about 70 wt.-% or at most about 50 wt.-% with respect to the whole composition.

Thus, typical ranges for the filler as component (F) include from about 5 to about 80 or from about 20 to about 70 or from about 35 to about 50 wt.-% with respect to the whole composition.

A wide variety of inorganic, hydrophilic or hydrophobic fillers may be employed such as silicas, aluminas, magnesias, titanias, inorganic salts, metallic oxides and glasses. It has been found to be possible to employ mixtures of silicone dioxides, including those derived from crystalline silicone dioxide, such as pulverized quartz (4-6 µm); amorphous silicone dioxides, such as a diatomaceous earth (4-7 µm); and silanated fumed silica, such as Cab-o-Sil TS-530 (160-240 $m^2/g$), manufactured by Cabot Corporation.

The sizes and surface areas of the foregoing materials can be adjusted to control the viscosity and thixotropicity of the resulting compositions. Some or all of the foregoing hydrophobic fillers may be superficially treated with one or more silanating agents, as known to those of ordinary skill in the art. Such silanating may be accomplished through use of known halogenated silanes or alkoxysilanes or silazanes. Such fillers can be present in amounts of from about 20 to about 80% by weight, especially about 25 to about 70 or about 30 to about 60 wt.-% of the material.

Among the fillers which can be used are fillers such as quartz, cristobalite, calcium silicate, diatomaceous earth, zirconium silicate, montmorillonite such as bentonite, zeolite, including molecular sieves such as sodium aluminium silicate, metal oxide powder such as aluminium or zinc oxide or their mixed oxides, barium sulphate, calcium carbonate, plaster, glass and plastic powder.

Suitable fillers are also pyrogenic or precipitated silicic acid and silica aluminium mixed oxides. Those filler are commercially available from companies like Wacker or Degussa under the trade names Aerosil™, HDK-H.

The above mentioned fillers can be hydrophobized, for example by treatment with organosilanes or siloxanes or by the etherification of hydroxyl groups to alkoxy groups. One type of filler or also a mixture of at least two fillers can be used. The particle distribution is preferably chosen such that there are no fillers with particle sizes of more than about 50 μm.

A combination of reinforcing and non-reinforcing fillers can be preferred. In this respect, the quantity of reinforcing fillers can range from about 0.1 to about 10 wt.-%, in particular from about 2 to about 7 wt.-% with respect to the whole composition.

Typical reinforcing fillers include fumed silica, carbon black and the like. They also can be surface treated and can improve mechanical properties like tensile strength or tear strength, of the cured silicone composition.

Pyrogenically-prepared highly-disperse silicic acids which have preferably been hydrophobized by surface treatment are preferred as reinforcing fillers. The surface treatment can be carried out, for example with dimethyldichlorosilane, hexamethyldisilazane, tetramethylcyclotetrasiloxane or polymethylsiloxane.

Preferred non-reinforcing fillers are quartzes, cristobalites and sodium aluminium silicates which can be surface-treated. The surface treatment can generally be carried out with the same methods as described in the case of the strengthening fillers.

Typical non-reinforcing fillers are quartz, precipitated silicas, diatomaceous earth, aluminas, magnesias, titanium dioxide, zirconium silicate, metallic oxides, and the like. These fillers can be surface treated, e.g. silanated, or non surface treated. Typical particle sizes are about 2 to about 10 μm.

According to another embodiment, the curable dental composition of the invention may contain organopolysiloxanes without reactive substituents as component (G) or part of component (G) even if the presence of such a component is not mandatory.

Non-reactive substituents include those which do not co-polymerize with the other components of the composition during the hardening process. These are preferably linear, branched or cyclic organopolysiloxanes where all silicon atoms are surrounded by oxygen atoms or monovalent hydrocarbon radicals with 1 to 18 carbon atoms which can be substituted or non-substituted. The hydrocarbon radicals can be methyl, ethyl, C3-C10 aliphatics, trifluoropropyl groups as well as aromatic C6-C12 radicals.

Polydimethylsiloxanes with trimethylsiloxy end groups are particularly preferred as a constituent of component (G). Component (G) can be used in an amount of about 0 to about 40 wt.-%, or about 0.1 to about 20 wt.-% or about 0.5 to about 15 wt.-%.

According to a further embodiment, the composition can also contain other additives e.g. as component (H) or part of component (H).

Those additives include retarders to modify the working and setting time (e.g. 3-methyl-1-butyne-3-ol or 1,1,3,3-tetramethyl-1,3-divinyl siloxane (VMO)), rheology modifiers (e.g. synthetic or natural waxes or polyethylene/propylene diacetates as described in EP 1 165 016 A1; corresponding to U.S. Pat. No. 6,677,393), inhibitors, pigments, dyes, plastizers (including paraffin oil or mineral oil), odorous substances, flavourings, stabilizers (including diphosphite(s) as described e.g. in WO 2007/001896 A2) or hydrogen scavenger etc. alone or in admixture.

The additive(s) can be present in an amount in the range of about 0.01 to about 90% by weight, or in the range of about 0.1 to about 40% by weight with respect to the cured composition.

To control the reactivity of the addition reaction and to prevent premature curing, it may be advantageous to add an inhibitor, which prevents the addition reaction for a specific period of time or slows the addition reaction down. Such inhibitors are known and described, e.g. in U.S. Pat. No. 3,933,880, the disclosure of which regarding such inhibitors and their preparation is expressly regarded as being part of the disclosure of the invention. Examples of such inhibitors include acetylenic unsaturated alcohols such as 3-methyl-1-butyne-3-ol, 1-ethynylcyclohexane-1-ol, 3,5-dimethyl-1-hexyne-3-ol and 3-methyl-1-pentyne-3-ol. Examples of inhibitors based an vinyl siloxane are 1,1,3,3-tetramethyl-1,3-divinyl siloxane, 1,3,5,7-tetravinyl-1,3,5,7-tetramethylcyclotetrasiloxane and poly-, oligo- and disiloxanes containing vinyl groups.

The composition may also contain a component useful for diminishing the presence or degree of hydrogen outgassing which may be typically generated as a result of the vinyl polymerization in the case of SiH curable composition. The composition thus may comprise a hydrogen scavenger such as finely divided platinum metal that scavenges for and takes up such hydrogen. The Pt metal may be deposited upon a substantially insoluble salt having a surface area of between about 0.1 and about 40 m$^2$/g. Suitable salts are Barium sulphate, barium carbonate and calcium carbonate of suitable particle sizes. Other substrates include diatomaceous earth, activated alumina, activated carbon and others. The inorganic salts are especially preferred to imply improved stability to the resulting materials incorporating them. Dispersed upon the salts is about 0.2 to about 2 parts per million of platinum metal, based upon the weight of the catalyst component. It has been found that employment of the platinum metal dispersed upon inorganic salt particles substantially eliminates or diminishes hydrogen outgassing during curing of dental silicones. Also Pd metal as described e.g. in U.S. Pat. No. 4,273,902 or Pd compounds as disclosed in to U.S. Pat. No. 5,684,060 can be employed.

The curable composition of the invention can also contain a polyethylene glycol derivate, (including polyethylene glycol dimethylether) having a chain-length e.g. equal or below about 1000 g/mol. Furthermore, the curable composition can also contain a polyol which can be chosen from the groups of carbohydrates, polyvinylalcohols, aliphatic di-, tri-, tetra-, penta-, or hexaols. Some specific examples are polyols available under the trade name Acclaim from Bayer Material Science or Pluracol from BASF AG.

According to one embodiment of the invention, the composition can comprise the individual components in the following amounts:

Component (A): from about 20 wt.-% to about 60 wt.-% or from about 25 wt.-% to about 55 wt.-% or from about 36 wt.-% to about 53 wt.-% with respect to the whole composition.

Component (B): from about 0.1 wt.-% to about 15 wt.-% or from about 1 wt.-% to about 10 wt.-% or from about 3 wt.-% to about 5 wt.-% with respect to the whole composition.

Component I: from about 0.001 wt.-% to about 0.1 wt.-% or from about 0.002 wt.-% to about 0.02 wt.-% or from about 0.005 wt.-% to about 0.01 wt.-% with respect to the whole composition.

Component (D): from about 0.1 wt.-% to about 60 wt.-% or from about 0.3 wt.-% to about 55 wt.-% or from about 0.5 wt.-% to about 50 wt.-% with respect to the whole composition.

Component (E): from about 0 wt.-% to about 30 wt.-% or from about 0.1 wt.-% to about 25 wt.-% or from about 0.2 wt.-% to about 20 wt.-% with respect to the whole composition.

Component (F): from about 0 wt.-% to about 80 wt.-% or from about 0.1 wt.-% to about 70 wt.-% or from about 0.5 wt.-% to about 50 wt.-% with respect to the whole composition.

Component (G): from about 0 wt.-% to about 40 wt.-% or from about 0 wt.-% to about 30 wt.-% or from about 0 wt.-% to about 20 wt.-% with respect to the whole composition.

Component (H): from about 0 wt.-% to about 90 wt.-% or from about 0.01 wt.-% to about 40 wt with respect to the whole composition.

The dental compositions according to the invention are typically multi component materials which comprise at least a curable base paste and a catalyst paste comprising a catalyst for curing at least part of the material of the base paste.

Accordingly, the components of the composition can be included in a kit, where the contents of the composition are packaged to allow for storage of the components until they are needed. When used, the components of the compositions can be mixed in the suitable amounts and clinically applied using conventional techniques.

Thus, the invention also relates to a kit of parts, comprising a base paste and a catalyst paste separated from each other before use, wherein the base paste comprises components (A) and (B), and the catalyst paste comprises component (C) or (C) and (A), and wherein component (D) is present either in the base paste or the catalyst paste or in the base paste and the catalyst paste. The same applies to component (E). The other optional components (F), (G), and (H) can be present in the base paste or the catalyst paste or in the base paste and the catalyst paste.

According to a certain embodiment of the invention, the surfactant is present in the base paste and the F-containing compound is present in the catalyst paste.

According to another embodiment of the invention, the base paste is essentially free of the F-containing compound and the catalyst paste is essentially free of the surfactant.

The volume ratios of catalyst paste and base paste can range from about 10:1 to about 1:10. Particularly preferred volume ratios of base paste to catalyst paste are about 1:1 and about 5:1 (5 parts of base paste to 1 part of catalyst paste).

Generally, mixing and dosing of the components can be performed manually, e.g., by spatula (strand-length comparison) or a manually operated pre-filled dual cartridge dispenser with static mixing tips, or automated, using one of the various available devices available for such an automated task, preferably one of the devices mentioned in EP 0 232 733 A1, U.S. Pat. No. 5,924,600, U.S. Pat. No. 6,135,631 or EP 0 863 088 A1 together with a dynamic mixing tip as mentioned in US 2004/0085854 or U.S. Pat. No. 6,244,740.

A further improvement of the handling properties of dental compositions can be seen in using an automatic mixing and metering systems for two-component compositions which have automatic conveying and mixing units, such as are described e.g. in U.S. Pat. No. 5,249,862, U.S. Pat. No. 5,286,105 and U.S. Pat. No. 5,332,122. The need for manual mixing of base pastes and catalyst pastes, above all when mixing larger quantities of material, can be eliminated, since this can take place automatically and within a short period of time.

The result is usually a homogeneous product which is essentially free of air bubbles. Commercially available devices are distributed by 3M ESPE under the brand Pentamix™ or Pentamix™ 2 or Pentamix™ 3.

In practice, the impression material can be syringed through a static or mechanical mixing device into an impression tray or onto patient's teeth or tissue and placed in the patient's mouth. After the impression material is set, the tray is removed from the patient's mouth and, in instances where the dental practitioner prepares the positive model, it may be preferable to pour the positive model material immediately after removal of the impression from the patient's mouth.

The invention also relates to a method of producing a curable composition comprising the step of combining an F-containing compound with a hardenable matrix or a composition comprising components (A), (B), (C), wherein components (A), (B) and (C) are as described herein.

Typically, after combining of the F-containing compound with the hardenable matrix or the individual components of the hardenable matrix, the components are mixed. The F-containing compound can be added to the other components of the composition from the very beginning of the production process or during or at the end of the production process.

The F-containing compound can also be applied as a pre-mixture with component (D) and/or component (F).

The dental material or composition can be used as impression material or for the production of (temporary or long term) crown and/or bridges. In the latter case, the composition is used as a mould to be filled with the (temporary or long term) crown and/or bridge material, which is typically based on polymerizable (meth)acrylates.

Another aspect of the invention, relates to a method of using the F-containing compound for enhancing the hydrophilicity of a hardenable composition, typically based on a dental composition as described above and comprising a surfactant as described above. The method typically includes the step of adding to or combining the F-containing compound with the other components for forming a hardenable matrix.

Features and advantages of this invention are further illustrated by the following examples, which are in no way intended to be limiting thereof. The particular materials and amounts thereof recited in these examples, as well as other conditions and details, should not be construed to unduly limit this invention. Unless otherwise indicated, all parts and percentages are on a weight basis, all water is deionized water, all molecular weights are weight average molecular weight and all measurements were done at ambient conditions (23° C.).

EXAMPLES

Measurements
Water Contact Angle Measurement of Un-Cured Paste

Test specimen preparation: For the preparation of test piece the mixed paste was subjected to an object slide and flattened and triturated by a second object slide in order to obtain a thin film. The test piece preparation was performed in that simplified way as the thickness of the film does not have a significant effect on the measured water contact angle (see G. Kugel, T. Klettke, J. A. Goldberg, J. Benchimol, R. D. Perry, S. Sharma, *J Prosthod.* 2007, 16, 84-92). Measurement: The object slide was placed on the table of a Drop Shape Analyse System DSA 10 (Krüss GmbH, Hamburg), a well known device for measuring contact angles. 5 µl of water were placed onto the surface of the specimen and an automatic contact angle measurement was started using standard software of the goniometer. Measuring time was at least about 10 s up to about 200 s.

The water contact angle was measured at different time periods after mixing of base paste and catalyst paste, especially after 40 and 60 s. The data (video sequences) were evaluated by the "circle fitting" method, another standard method for data evaluation (see G. Kugel, T. Klettke, J. A. Goldberg, J. Benchimol, R. D. Perry, S. Sharma, *J. Prosthod.* 2007, 16, 84-92).

$\Theta_{10s}$ is the angle obtained 10 s after placing the water drop on the surface.

$\Theta_{0s}$ is the angle obtained immediately after placing the water drop on the surface (initial water contact angle).

Determination of Setting Time

The setting time of the compositions was determined by measuring the viscosity in dependence on the time at 33° C. by using a MDR 2000 rheometer from Alpha instruments under aerobic conditions at 50% humidity. The setting time was determined as the $t_{90}$ value, at which 90% of the final viscosity was achieved. Another characteristic size is the $t_5$ value, at which 5% of the final viscosity was present. Until this time the composition can be assumed to be almost free of network formation (curing).

Tensile Strength and Elongation at Break

The tensile strength and elongation of the compositions was determined according to DIN 53504. The tensile strength is given in MPa and the elongation in % of the original length. Tensile strength and elongation data were evaluated by tearing six I-shaped specimens with a central unit of 20 mm×4 mm×2 mm in a Zwick Z020 Universal testing machine. Base and catalyst pastes were mixed through a static mixer (SulzerMixpac Comp.) and filled into a brass mould. After 3 h at 23° C. the specimen were removed, six measurements were made and the mean value determined (speed 200 mm/min).

Linear Dimensional Change

The linear dimensional change of the compositions was determined according to ISO 4823 and is given in %.

Viscosity

The viscosity was measured at 23° C. using a Haake Rotovisco 1 device with a plate/plate system (diameter 20 mm) and a slit of 0.2 mm. The viscosity values (Pas) and share stress values (Pa) are recorded for each share rate ($\square$) starting from 10 1/s to 100 1/s in 10 1/s and/or 5 1/s steps. For each share rate, a delay of 5 seconds was used before collecting data. The above mentioned method of measurement corresponds essentially to DIN 53018-1.

Shelf Life Time Determination

For the determination of the shelf life time, the catalyst paste B containing 1.5 wt.-% of HFPO-OMe (Mn=1008), HFPO-amidol (Mn=1032) 1H,1H-Perfluor-3,6,9-trioxatridecan-1-ol, Silwet L-77 or Zonyl FSO-100, respectively, was filled in a conventional foil bag (3M ESPE) and stored at 70° C. After the storage time given in Table 8 below, the setting time was determined according to the method described above by mixing the stored catalyst paste with an at room temperature stored base paste (according to base paste formula A, see below).

HFPO-OMe: $CF_3-(CF_2)_2-(O-CF(CF_3)-CF_2)_z-O-CF(CF_3)-COOCH_3$

HFPO-amidol: $CF_3-(CF_2)_2-(O-CF(CF_3)-CF_2)_z-O-CF(CF_3)-CONHCH_2CH_2OH$

General Description—Preparation of Composition

The base and the catalyst paste used hereafter have been prepared in a vacuum kneader by mixing the respective components to a homogenous paste.

Base Paste Formula A:

| | |
|---|---|
| Mixture of vinyl terminated polydimethylsiloxane (7,900 mPas) | 50.5% (weight) |
| Poly(methyl)(hydrogen)siloxane (75 mPas) | 11.9% (weight) |
| Pyrogenic silica (hydrophobized, 100 m$^2$/g) | 5.9% (weight) |
| Crystalline SiO$_2$ filler (<20 μm) | 31.7% (weight) |

Catalyst Paste Formula A (Regular Setting Material):

| | |
|---|---|
| Mixture of vinyl terminated polydimethylsiloxane (5,800 mPas) | 48.6% (weight) |
| Tetraallylsilane | 0.5% (weight) |
| Platin tetramethyldivinyldisiloxane (VMO) complex 1.3 wt.-% Pt in silicone oil | 0.2% (weight) |
| Platin tetramethyldivinyldisiloxane complex 1.3 wt.-% Pt in silicone oil containing in addition 4% of VMO | 1.4% (weight) |
| Palladium chloride dispersion in vinyl terminated polydimethylsiloxane (2,000 mPas) | 0.1% (weight) |
| Pyrogenic silica (hydrophobized, 100 m$^2$/g) | 5.7% (weight) |
| Crystalline SiO$_2$ filler (<20 μm) | 42.7% (weight) |
| Pigment dispersion in polydimethylsiloxane (30,000 to 100,000 mPas) | 0.8% (weight) |

Catalyst Paste Formula B (Fast Setting Material):

Catalyst paste formula B differs from catalyst paste formula A with respect to the platinum complex. The other components were the same.

| | |
|---|---|
| Platin tetramethyldivinyldisiloxane (VMO) complex 1.3 wt.-% Pt in silicone oil containing in addition 0.3% VMO | 1.12% (weight) |
| Platin tetramethyldivinyldisiloxane complex 1.3 wt.-% Pt in silicone oil containing in addition 4% of VMO | 0.48% (weight) |

X wt.-% of surfactant and Y wt.-% of the F-containing compound were added to the base paste A and/or the catalyst pastes A or B, respectively, and kneaded under vacuum for about 30 min to obtain a homogenous paste (Table 1).

The base paste and catalyst paste were filled in a dual chamber cartridge (SulzerMixpac Comp.), volume ratio 1:1, equipped with a static mixing tip (SulzerMixpac Company). The pastes were extruded from the cartridge and mixed using a hand mixing apparatus (3M ESPE Comp.).

The un-cured and cured compositions were tested with respect to their wetting behaviour (Tables 2-8 and 11-19) and the cured compositions with respect to their physical parameters (Table 9). The storage stability of the catalyst paste containing 1.5 wt.-% of surfactant or F-containing compound was tested and the results are summarized in Table 10.

TABLE 1

| | Base paste A | | Catalyste paste A | | F-containing compound, surfactant used |
|---|---|---|---|---|---|
| | F-containing compound | surfactant | F-containing compound | surfactant | |
| regular setting material $t_5/t_{90}$ = 2.03/3.56 [min] | | | | | |
| Example 1 | 3.5 | 3.0 | — | — | HFPO-OMe [c], Silwet L-77 [a] |
| Example 2 | 3.5 | 3.0 | — | 1.5 | HFPO-OMe [c], Silwet L-77 [a] |
| Example 3 | 3.5 | 3.0 | 1.5 | — | HFPO-OMe [c], Silwet L-77 [a] |
| Example 4 | 3.5 | 3.0 | 1.5 | 1.5 | HFPO-OMe [c], Silwet L-77 [a] |
| Example 5 | 3.5 | 3.0 | — | — | HFPO-OMe [c], Carbosilantensid [b] |
| C. Example V1 | — | 3.0 | — | — | Silwet L-77 [a] |
| C. Example V2 | — | 3.0 | — | — | Carbosilantensid [b] |
| C. Example V3 | 3.5 | — | — | — | HFPO-OMe [c] |
| C. Example V4 | 3.5 | — | — | — | Zonyl FSO-100 [f] |
| Fast setting material $t_5/t_{90}$ = 1.48/2.48 [min] | | | | | |
| Example 6 | 3.5 | 3.0 | — | — | HFPO-OMe [c], Silwet L-77 [a] |
| Example 7 | 3.5 | 3.0 | 1.5 | — | HFPO-OMe [c], Silwet L-77 [a] |
| Example 8 | 3.5 | 3.0 | — | — | HFPO-Amidol (1032) [d], Silwet L-77 [a] |
| Example 9 | 3.5 | 3.0 | — | — | 1H,1H-Perfluor-3,6,9-trioxatridecan-1-ol [e], Silwet L-77 [a] |
| Example 10 | 2.0 | 3.0 | — | — | 1H,1H-Perfluor-3,6,9-trioxatridecan-1-ol [e], Silwet L-77 [a] |
| Example 11 | 5.0 | 3.0 | — | — | 1H,1H-Perfluor-3,6,9-trioxatridecan-1-ol [e], Silwet L-77 [a] |
| Example 12 | — | 3.0 | 1.5 | — | 1H,1H-Perfluor-3,6,9-trioxatridecan-1-ol [e], Silwet L-77 [a] |
| Example 13 | — | 3.0 | 3.5 | — | 1H,1H-Perfluor-3,6,9-trioxatridecan-1-ol [e], Silwet L-77 [a] |
| Example 14 | 2.0 | 3.0 | 1.5 | — | 1H,1H-Perfluor-3,6,9-trioxatridecan-1-ol [e], Silwet L-77 [a] |
| C. Example V5 | 3.5 | 3.0 | — | — | Zonyl FSO-100 [f], Silwet L-77 [a] |
| C. Example V6 | — | 3.0 | — | — | Silwet-L77 [a] |

C. Example means comparative example.
[a] Silwet L-77 (Momentive Corp.)
[b] Carbosilantenside can be obtained as described in Production Example 2 in U.S. Pat. No. 5,750,589.
[c] HFPO (hexa fluor propylene oxide) oligomers: Dyneon LCC The methyl ester of the HFPO-oligomer (HFPO-OMe; Mn = 1008 g/mol) was obtained from Dyneon LCC and can be synthesized as described e.g. in WO2004/060956 A1.
[d] The HFPO-amidol is obtainable according to the description in WO2004/060964 A1 and was applied in different mean molecular weights (Mn) in g/mol, which are given in brackets.
[e] 1H,1H-Perfluor-3,6,9-trioxatridecan-1-ol is obtainable from Apollo Scientific Ltd.
[f] Zonyl FSO-100: ethoxylated perfluoroalcanol (obtainable from Aldrich or Du Pont) having an HLB-value of 11.5 according to WO 2007/080071 A2 and technical data sheet.

Table 2 shows the water contact angles 40 s and 60 s after mixing of base paste and catalyst paste for the Examples given in Table 1 (measured according to the description above with respect to Water contact measurement of un-cured paste).

TABLE 2

| | Water contact angle $\Theta_{10 s}$ (°); 40 s after mixing | Water contact angle $\Theta_{10 s}$ (°); 60 s after mixing |
|---|---|---|
| Example 1 | 40 | <2 |
| Example 2 | 2 | 3 |
| Example 3 | 76 | <5 |
| Example 4 | 3 | 3 |
| Example 5 | 49 | 12 |
| C. Example V1 | 70 | 70 |
| C. Example V2 | 60 | 57 |
| C. Example V3 | 96 | 97 |
| C. Example V4 | 83 | 65 |
| Example 6 | 6 | 2 |
| Example 7 | 70 | <6 |
| Example 8 | 5 | 6 |
| Example 9 | 10 | 7 |
| Example 10 | 51 | 51 |
| Example 11 | 60 | 65 |

TABLE 2-continued

|  | Water contact angle $\Theta_{10\,s}$ (°); 40 s after mixing | Water contact angle $\Theta_{10\,s}$ (°); 60 s after mixing |
|---|---|---|
| Example 12 | 44 | 51 |
| Example 13 | 59 | 71 |
| Example 14 | 57 | 67 |
| C. Example V5 | 4 | 2 |
| C. Example V6 | 60 | 56 |

Another feature determined was the time a water drop needs to reach a water contact angle of 10° after mixing the composition (t ($\theta\theta = 10°$) in s). This time mirrors the clinical situation and reflects the ability to wet the saliva fast and efficient and, thus, to realize an effective water extrusion and provide sufficient detail accuracy. The time that a drop needs to reach a water contact angle of 10° at different times after mixing of base paste and catalyst paste is summarized in Table 3.

TABLE 3

|  | 40 s | 60 s |
|---|---|---|
| Example 1 | 17 | 5 |
| Example 2 | 2 | 3 |
| Example 3 | 13 | 4 |
| Example 4 | 2 | 1 |
| Example 5 | n.d.[a] | 10 |
| C. Example V1 | n.d.[a] | n.d.[a] |
| C. Example V2 | n.d.[a] | n.d.[a] |
| C. Example V3 | n.d.[a] | n.d.[a] |
| C. Example V4 | n.d.[a] | n.d.[a] |
| Example 6 | 9 | 4 |
| Example 7 | 18 | 2 |
| Example 8 | 3 | 2 |
| Example 9 | 4 | 3 |
| Example 10 | n.d.[a] | n.d.[a] |
| Example 11 | n.d.[a] | n.d.[a] |
| Example 12 | n.d.[a] | n.d.[a] |
| Example 13 | n.d.[a] | n.d.[a] |
| Example 14 | n.d.[a] | n.d.[a] |
| C. Example V5 | 3 | 2 |

[a] water contact angle during measurement time always above 10°

The initial contact angles ($\theta_{0s}$ in degrees) obtained for Examples 9-14 are summarized in Table 4 and the initial contact angle of Example 14 in dependence on the time after mixing is summarized in Table 5.

TABLE 4

|  | 40 s | 60 s |
|---|---|---|
| Example 9 | 70° | 65° |
| Example 10 | 63° | 57° |
| Example 11 | 67 | 73 |
| Example 12 | 52° | 57° |
| Example 13 | 82° | 83° |
| Example 14 | 73° | 75° |

TABLE 5

| Time after mixing in s | $\theta_{0s}$ |
|---|---|
| 12 | 76° |
| 20 | 75° |
| 40 | 73° |
| 60 | 75° |

Example 15

Base paste A was mixed according to the general procedure described above with 3.0 wt-% Silwet L-77 and 3.5 wt.-% of perfluoro-3,5,7,9-tetraoxadecanoic acid ethyl ester[x]. The wetting behaviour was determined as described above 20 and 40 seconds after mixing of base paste and catalyst paste B and is summarized in Table 6.

[x] Perfluoro-3,5,7,9-tetraoxadecanoic acid was purchased from Anles St. Petersburg. The amidol derivative thereof was synthesized according to the procedure described for the HFPO-amidol in WO2004/060964 A1 and the ethyl ester derivative was produced by known esterification methods.

Example 16

Base paste A was mixed according to the general procedure described above with 3.0 wt-% Silwet L-77 and 3.5 wt.-% of perfluoro-3,5,7,9-tetraoxadecanoic acid amidol[x]. The wetting behaviour was determined as described above 20 and 40 seconds after mixing of base paste and catalyst paste B. The results are summarized in Table 6.

Example 17

Base paste A was mixed according to the general procedure described above with 3.0 wt-% Silwet L-77 and 3.5 wt.-% of Fomblin™ YR-1800[y]. The wetting behaviour was determined as described above 20 and 40 seconds after mixing of base paste and catalyst paste B. The results are summarized in Table 6.

[y] Fomblin™ YR-1800: Solvay Solexis or ABCR (Karlsruhe, Germany).

TABLE 6

|  | 20 | | | 40 | | |
|---|---|---|---|---|---|---|
| Example | 15 | 16 | 17 | 15 | 16 | 17 |
| $\theta_{0s}$ in degree | 74 | 35 | 117 | 70 | 34 | 120 |
| $\theta_{10s}$ in degree | 65 | <4 | 58 | 9 | <3 | 10 |
| t ($\theta = 10°$) in s | >30 | 1 | >30 | 7 | 1 | 9 |

Example 18

Base paste A was mixed according to the general procedure described above with 3.0 wt-% Silwet L-77 and 3.5 wt.-% of Vinyl-Si(Me)$_2$-functionalized HFPO-amidol[z]. The wetting behaviour was determined as described above 20 and 40 seconds after mixing of base paste and catalyst paste B. The results are summarized in Table 7.

[z] The Vinyl-Si(Me)2-functionalized HFPO-amidol (Mn=1121) was prepared according to the following procedure: 25.93 g (25 mmol) 2-Hydroxyethylamido-HFPO-Oligomer (Molecular Weight 1032) were mixed under nitrogen with 2.78 g (27.5 mmol) triethylamine. At ambient temperature 3.32 g (27.5 mmol) of Vinyl-dimethyl-chlorosilane are slowly added while temperature rises to about 40° C. and a white solid precipitates. After 16 hours stirring at ambient temperature the reaction mixture is diluted with 100 ml toluene, filtrated and the solvent removed from the two phased mother liquor. Yield: 20 g (71%) of a clear slightly viscous product. According to $^1$H NMR silylation was complete.

Example 19

Base paste A was mixed according to the general procedure described above with 3.0 wt-% Silwet L-77 and 1.5 wt.-% of Vinyl-Si(Me)$_2$-functionalized HFPO-amidol[z]. The wetting behaviour was determined as described above 20 and 40 seconds after mixing of base paste and catalyst paste B. The results are summarized in Table 7.

TABLE 7

| | 20 | | 40 | |
| --- | --- | --- | --- | --- |
| Example | 18 | 19 | 18 | 19 |
| $\theta_{0\,s}$ in degree | 39 | 104 | 110 | 108 |
| $\theta_{10\,s}$ in degree | 17 | 15 | 17 | 12 |
| t ($\theta = 10°$) in s | >30 | 20 | 20 | >11 |

Comparative Example 7

CE V7

Base paste A was mixed according to the general procedure described above with 3.5 wt-% HFPO-amidol and 0.25 wt.-% of polyethylene glycol dimethylether (M=250). The wetting behaviour was determined as described above 40 and 60 seconds after mixing of base paste and catalyst paste B and is summarized in Table 8.

Comparative Example 8

CE V8

Base paste A was mixed according to the general procedure described above with 3.5 wt-% 1H,1H-Perfluoro-3,6,9-trioxa-tridecan-1-ol. The wetting behaviour was determined as described above 20 and 40 seconds after mixing of base paste and catalyst paste B and is summarized in Table 8.

TABLE 8

| | 20 | | 40 | | 60 | |
| --- | --- | --- | --- | --- | --- | --- |
| Example | CE V7 | CE V8 | CE V7 | CE V8 | CE V7 | CE V8 |
| $\theta_{0\,s}$ in degree | — | 120 | 130 | 136 | 127 | — |
| $\theta_{10\,s}$ in degree | — | 88 | 104 | 103 | 91 | — |

A comparison of other physical parameters of exemplified cured composition containing either 1.75 wt.-% HFPO-OMe (Example 7) or Zonyl™ FSO-100 (Comparative Example 5) and 1.5 wt.-% Silwet L-77 is shown in Table 9.

TABLE 9

| | Example 7 | C. Example 5 |
| --- | --- | --- |
| Tensile strength [MPa] | 4.76 | 4.50 |
| Elongation at break [%] | 262 | 242 |
| viscosity base paste [Pas]; $\gamma = [50\ 1/s]$ | 17.219 | 18.276 |

For comparison:
Viscosity of base paste A (without containing Silwet L-77): 23.558 Pas
Viscosity of base paste A containing 3.0 wt.-% Silwet L-77: 18.800 Pas
Viscosity of composition of Example 22 (containing Silwet L-77, HFPO acid methyl ester (Mn=1008) and 1H,1H-Perfluor-3,6,9-trioxatridecan-1-ol): 15.604 Pas As can be seen from Table 9, the addition of HFPO acid methyl ester (instead of Zonyl FSO-100) leads to a composition having a lower viscosity (i.e. a better flowing behavior) without jeopardizing tensile strength and elongation at break.

In Table 10 the shelf life times of catalyst paste B containing 1.5 wt.-% of surfactant or F-containing compound at 70° C. are summarized. The values indicate the working time/setting time [min] after storing the composition at 70° C. for various days.

TABLE 10

| T = 70° C. | Start | 2 d | 4 d | 7 d | 14 d | 21 d | 28 d | 35 d | 42 d |
| --- | --- | --- | --- | --- | --- | --- | --- | --- | --- |
| 1H,1H-Perfluoro-3,6,9-trioxatridecan-1-ol | 0.93/2.16 | — | — | 1.04/2.41 | 1.01/2.31 | 5.31/9.08 | 6.65/9.84 | 3.01/6.81 | 4.11/5.82 |
| HFPo-OMe (Mn = 1008) | 1.20/2.79 | 1.41/2.79 | 5.65/>10 | No set | No set | No set | No set | No set | No set |
| HFPO-amidol (Mn = 1032) | 1.01/1.89 | 1.17/2.02 | — | 0.86/2.27 | 1.03/2.70 | — | 1.02/7.60 | No set | No set |
| Zonyl FSO-100 | 1.74/5.46 | No set | No set | No set | No set | No set | No set | No set | No set |
| Silwet L-77 | 0.94/2.34 | 1.46/3.09 | 2.67/5.74 | No set | No set | No set | No set | No set | No set |
| Catalyst paste B | 1.48/2.48 | — | — | 1.15/2.18 | 6.28/9.54 | No set | No set | No set | No set |

Example 20

Base paste A and catalyst paste B were mixed according to the general procedure described above with 3.0 wt-% Silwet L-77 and 2.0 wt-% of HFPO-OMe and 1.5% of 1H,1H-perfluor-3,6,9-trioxatridecan-1-ol. The wetting behaviour was determined as described above 30, 40 and 60 seconds after mixing of base paste and catalyst paste and can be taken from Table 11.

Example 21

Base paste A and catalyst paste B were mixed according to the general procedure described above with 3.0 wt-% Silwet L-77 and 2.5 wt.-% of HFPO-OMe and 1.0% of 1H,1H-perfluor-3,6,9-trioxatridecan-1-ol. The wetting behaviour was determined as described above 20, 30 and 40 seconds after mixing of base paste and catalyst paste. The results summarized in Table 11.

The initial contact angles and the water contact angles as well as the time a water drop needs to reach a contact angle of 10° are summarized in Table 11. These results reveal that using a mixture of different F-containing compounds might even improve the wetting behaviour of the curable composition.

TABLE 11

| Example | 20 seconds | | | 30 seconds | | 40 seconds | | | 60 seconds | |
|---|---|---|---|---|---|---|---|---|---|---|
| | CE 5 | 20 | 21 | 20 | 21 | CE 5 | 20 | 21 | 20 | 21 |
| $\theta_{0\,s}$ in degree | 109 | — | 27 | 68 | 30 | 67 | 56 | 36 | 25 | — |
| $\theta_{10\,s}$ in degree | 7 | — | 6 | 48 | 6 | 4 | 46 | 5 | 6 | — |
| t ($\theta$ = 10°) in s | 6 | — | 4 | n.d. | 4 | 4 | n.d. | 3 | 4 | — |

FIG. 1 shows the time dependency of the water contact angle of exemplified compositions measured at different time periods after mixing of base paste and catalyst paste.

Example 22

Base paste A was mixed according to the general procedure described above with 3.0 wt-% Silwet L-77 and 0.50 wt.-% of HFPO-OMe and 1.0 wt.-% of 1H,1H-perfluor-3,6,9-trioxatridecan-1-ol. The wetting behaviour was determined as described above 20 and 40 seconds after mixing of base paste and catalyst paste B. The results are summarized in Table 12.

Example 23

Base paste A was mixed according to the general procedure described above with 3.0 wt-% Silwet L-77 and 0.25 wt.-% of HFPO-amidol (Mn=1032) and 0.75 wt.-% of 1H,1H-perfluor-3,6,9-trioxatridecan-1-ol. The wetting behaviour was determined as described above 20 and 40 seconds after mixing of base paste and catalyst paste. The results are summarized in Table 12.

TABLE 12

| | 20 seconds | | 40 seconds | |
|---|---|---|---|---|
| Example | 22 | 23 | 22 | 23 |
| $\theta_{0\,s}$ in degree | 30 | 23 | 24 | 20 |
| $\theta_{10\,s}$ in degree | 16 | 12 | 9 | 10 |
| t ($\theta$ = 10°) in s | 17 | 15 | 7 | 9 |

Example 24

Base paste A was mixed according to the general procedure described above with 3.0 wt-% Silwet L-77 and 0.25 wt.-% of HFPO-OMe and 1.00 wt.-% of 1H,1H-perfluor-3,6,9-trioxatridecan-1-ol and 0.25 wt.-% polyethylene glycol-dimethylether (Mn=250 g/mol).[r] The wetting behaviour was determined as described above 20 and 40 seconds after mixing of base paste and catalyst paste B. The results are summarized in Table 12.
[r]polyethylene glycol dimethylether (Mn=250 g/mol) was obtained from Aldrich.

Example 25

Base paste A was mixed according to the general procedure described above with 3.0 wt-% Silwet L-77 and 0.65 wt.-% of HFPO-amidol (Mn=1032) and 0.25 wt.-% polyethylene glycol-dimethylether (Mn=250 g/mol). The wetting behaviour was determined as described above 20 and 40 seconds after mixing of base paste and catalyst paste. The results are summarized in Table 13.

Example 26

Base paste A was mixed according to the general procedure described above with 3.0 wt-% Silwet L-77 and 0.15 wt.-% of HFPO-amidol (Mn=1032) and 0.50 wt.-% of 1H,1H-perfluor-3,6,9-trioxatridecan-1-ol and 0.25 wt.-% polyethylene glycol-dimethylether (Mn=250 g/mol). The wetting behaviour was determined as described above 20 and 40 seconds after mixing of base paste and catalyst paste. The results are summarized in Table 13.

Example 27

Base paste A was mixed according to the general procedure described above with 3.0 wt-% Silwet L-77 and 0.65 wt.-% of Vinyl-Si(Me)$_2$-functionalized HFPO-amidol (Mn=1032) and 0.25 wt.-% polyethylene glycol dimethyl ether (Mn=250). The wetting behaviour was determined as described above 20 and 40 seconds after mixing of base paste and catalyst paste B. The results are summarized in Table 13.

TABLE 13

| | 20 seconds | | | | 40 seconds | | | |
|---|---|---|---|---|---|---|---|---|
| Example | 24 | 25 | 26 | 27 | 24 | 25 | 26 | 27 |
| $\theta_{0\,s}$ in degree | 22 | 114 | 22 | 113 | 24 | 125 | 25 | 103 |
| $\theta_{10\,s}$ in degree | 10 | 9 | 11 | 11 | 9 | 8 | 9 | 9 |
| t ($\theta$ = 10°) in s | 9 | 9 | 12 | 12 | 7 | 5 | 6 | 9 |

Example 28

Base paste A was mixed according to the general procedure described above with 3.0 wt-% Silwet L-77 and 0.65 wt.-% of HFPO-amidol (Mn=1032) and 0.15 wt.-% of DDA[s]. The wetting behaviour was determined as described above 20 and 40 seconds after mixing of base paste and catalyst paste B. The results summarized in Table 14.
[s]Copolymer of tetrahydrofuran and ethylene oxide end-capped with acetoxy groups; Mn ~6000. DDA was synthesized as described in EP 1 165 016 B1.

Example 29

Base paste A was mixed according to the general procedure described above with 3.0 wt-% Silwet L-77 and 0.65 wt.-% of Vinyl-Si(Me)$_2$-functionalized HFPO-amidol and 0.15 wt.-% of DDA. The wetting behaviour was determined as described above 20 and 40 s after mixing of base paste and catalyst paste B. The results are summarized in Table 14.

TABLE 14

| | 20 | | 40 | |
|---|---|---|---|---|
| Example | 28 | 29 | 28 | 29 |
| $\theta_{0\,s}$ in degree | 118 | 104 | 107 | 117 |
| $\theta_{10\,s}$ in degree | 11 | 15 | 11 | 11 |
| t ($\theta$ = 10°) in s | 12 | 20 | 13 | 11 |

Example 30

Base paste A was mixed according to the general procedure described above with 3.0 wt-% Silwet L-77 and 1.5 wt.-% of HFPO-amidol (Mn=1266) and 0.25 wt.-% of Brij™ 30 (Croda Int. PLC; polyalkylene(4)laurylether; M=362 g/mol).

Example 31

Base paste A was mixed according to the general procedure described above with 3.0 wt-% Silwet L-77 and 1.5 wt.-% of HFPO-amidol (Mn=1266) and 0.25 wt.-% of Triton™ X-100 (Union Carbide Corp.; octylphenol ethyoxylate; M=647 g/mol).

Example 32

Base paste A was mixed according to the general procedure described above with 3.0 wt-% Silwet L-77 and 1.5 wt.-% of HFPO-amidol (Mn=1266) and 0.15 wt.-% of Breox™ 50A20 (Cognis Corp.; EO/PO copolymer; viscosity: 19 cSt. at 40° C.).

Example 33

Base paste A was mixed according to the general procedure described above with 3.0 wt-% Silwet L-77 and 1.5 wt.-% of HFPO-amidol (Mn=1266) and 0.15 wt.-% of Acclaim™ 12000 (Bayer Corp.; polyether polyol; M=11,200 g/mol).

The wetting behaviour of Example 30-33 was determined as described above 20 and 40 seconds after mixing of base paste and catalyst paste B and is summarized in Table 15.

TABLE 15

| | 20 | | | | 40 | | | |
|---|---|---|---|---|---|---|---|---|
| Example | 30 | 31 | 32 | 33 | 30 | 31 | 32 | 33 |
| $\theta$ (0 s) | 109 | 113 | 101° | 114 | 115 | 112 | 104 | 114 |
| $\theta$ (10 s) | 16 | 18 | 13° | 15 | 17 | 14 | 12 | 17 |
| t (10°) | >30 | >30 | 20 | >30 | 23 | >30 | 17 | >30 |

Comparative Example 9

Base paste A was mixed according to the general procedure described above with 3.0 wt-% Silwet L-77 and 3.5 wt.-% of Zonyl FSN-100 (obtainable from Aldrich or DuPont). The wetting behaviour was determined as described above 20 and 40 seconds after mixing of base paste and catalyst paste B and is summarized in Table 16.

TABLE 16

| | 20 | 40 | 60 |
|---|---|---|---|
| $\theta_{0\,s}$ in degree | 122 | 105 | 113 |
| $\theta_{10\,s}$ in degree | 52 | 31 | 24 |
| t ($\theta$ = 10°) in s | >30 | >30 | >30 |

Example 34

Base paste A was mixed according to the general procedure described above with 3.0 wt-% Silwet L-77 and 1.5 wt.-% of HFPO-amidol (Mn=1032). The wetting behaviour was determined as described above 20 and 40 seconds after mixing of base paste and catalyst paste B. The results summarized in Table 17.

Comparative Example 10

Base paste A was mixed according to the general procedure described above with 3.0 wt-% Silwet L-77 and 1.5 wt.-% of Zonyl FSO-100. The wetting behaviour was determined as described above 20 and 40 seconds after mixing of base paste and catalyst paste B. The results are summarized in Table 17.

TABLE 17

| | 20 | | 40 | |
|---|---|---|---|---|
| Example | 34 | C.E. V10 | 34 | C.E. V10 |
| $\theta_{0\,s}$ in degree | 109 | 100 | 122 | 119 |
| $\theta_{10\,s}$ in degree | 15 | 51 | 12 | 66 |
| t ($\theta$ = 10°) in s | n.d. | >30 | 15 | 20 |

Setting times of material obtained by mixing of catalyst paste B with base pastes according to examples (see Table 1 and example 34, 35 C.E. V9) described before containing different fluorinated additives in various amounts are summarized in Table 18. The results in table 18 clearly reveal that with the enclosed additives of this investigation show $t^{90}$ values below 5 min, thus, not leading to a significant deceleration of the setting time. The setting time was determined as described above.

TABLE 18

| | $t^{90}$ [min] |
|---|---|
| 7 | 4.99 |
| 8 | 2.41 |
| 9 | 2.58 |
| 34 | 2.44 |
| C.E V6 | 2.48 |
| C.E. V5 | 6.13 |
| C.E. V9 | 6.48 |
| C.E. V10 | 5.16 |

Condensation-Crosslinking Silicone Compositions

Example 35

The base paste of the condensation-crosslinking Xantopren™ Blue L (Heraeus Kulzer) was mixed according to the general procedure described above with 3.0 wt-% Silwet L-77 and 1.5 wt.-% of HFPO-amidol (Mn=1032). The wetting behaviour was determined as described above 40 and 60 seconds after mixing of base paste and the Universal Activator paste (Heraeus Kulzer) and is summarized in Table 19.

Example 36

The base paste of the condensation-crosslinking Xantopren™ Blue L (Heraeus Kulzer) was mixed according to the general procedure described above with 3.0 wt-% Silwet L-77 and 3.5 wt.-% of HFPO-OMe. The wetting behaviour was determined as described above 40 and 60 seconds after mixing of base paste and the Universal Activator paste (Heraeus Kulzer) and is summarized in Table 19.

TABLE 19

| | 60 | |
|---|---|---|
| Example | 35 | 36 |
| $\theta_{0\,s}$ in degree | 30 | 106 |
| $\theta_{10\,s}$ in degree | 14 | 8 |
| t ($\theta$ = 10°) in s | >30 | 5 |

The invention claimed is:
1. A curable dental composition comprising:
a) a curable organopolysiloxane polymer as component (A);

b) a crosslinker compound capable of crosslinking said organopolysiloxane polymer, as component (B);

c) a catalyst capable of catalyzing a crosslinking reaction of component (A) and component (B), as component (C);

d) a surfactant as component (D), wherein the surfactant is selected from the group consisting of:

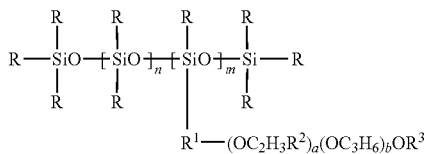

$R^1$—$(OC_2H_3R^2)_a(OC_3H_6)_bOR^3$ where each R is independently a monovalent hydrocarbyl radical with 1 to 22 C-atoms $R^1$ is a divalent hydrocarbylene radical 1 to 26 C-atoms, each $R^2$ is independently hydrogen or a lower hydroxyalkyl radical, $R^3$ is hydrogen or a monovalent hydrocarbyl radical with 1 to 22 C-atoms, n and b are independently greater than or equal to 0, and m and a are independently greater than or equal to 1;

Q-P—$(OC_nH_{2n})_x$—OT,

Q being $R_3$—Si— or $R_3$—Si—$(R'—SiR_2)_a$—R'—SiR''$_2$, where each R in the molecule can be the same or different and stands for an aliphatic $C_1$-$C_{18}$, a cycloaliphatic $C_6$-$C_{12}$ or an aromatic $C_6$-$C_{12}$ hydrocarbon radical, which can optionally be substituted by halogen atoms; R' is a $C_1$-$C_{14}$ alkylene group; R" is R in the case of a≠0 or is R or $R_3SiR'$ in the case of a=0, and a=0 to 2; P stands for a $C_2$-$C_{18}$ alkylene group, or A-R''', where A represents a $C_2$-$C_{18}$ alkylene group and R''' a functional group from the following list: —NHC(O)—, —$(CH_2)_{n-1}$—, —NHC(O)C(O)—, —NHC(O)$(CH_2)_vC(O)$—, —OC(O)—, —OC(O)$(CH_2)_{n-1}$—, —OC(O)C(O)—, —OC(O)$(CH_2)_vC(O)$—, —OCH$_2$CH(OH)CH$_2$OC(O)$(CH_2)_{n-1}$—, —OCH$_2$CH(OH)CH$_2$OC(O)$(CH_2)_vC(O)$— with v=1 to about 12; T is H or stands for a C1 to C4 alkyl radical or a C1 to C4 acyl radical; x stands for a number from 1 to about 200 and n stands for an average number from 1 to about 6; and mixtures thereof;

e) a F-containing compound as component (E), wherein F-containing compound is selected from the group consisting of:

(i) $T_1$-X—[(O—$CF_2$—$CF_2)_u$—(O—$CF_2)_v$—(O—CF($CF_3$)—$CF_2)_w$—(O—$CF_2$—$CF_2$—$CF_2)_x$—O]—X-$T_2$, with u=0 to 8, v=0 to 8, w=0 to 8 and x=0 to 8 and u+v+w+x≧1, and wherein X is selected from the group consisting of —$(CF_2)_{1-6}$—, —CF($CF_3$)—, and —CHF—$CF_2$—;

(ii) Rf—$(O)_t$—CHF—$(CF_2)_x$-T, with t=0 or 1, x=0 or 1, and Rf being a linear or branched per- or partly fluorinated alkyl chain, wherein the alkyl chain can be interrupted by one or more O atoms, with the proviso that when t is 0, Rf is a linear or branched per- or partly fluorinated alkyl chain interrupted by at least one oxygen atoms;

(iii) Rf—$(OcF_2)_m$—O—$CF_2$-T, with m=1 to about 6 and Rf being a linear or branched per- or partly fluorinated alkyl chain, wherein the alkyl chain can be interrupted by O atoms;

(iv) $CF_3$—$(CF_2)_2$—$(OCF(CF_3)$—$CF_2)_z$—O-L-T, with z=1, 2, 3, 4, 5, 6, 7 or 8, and L having a structure selected from the group consisting of —CF($CF_3$)—, —$CF_2$—, and —$CF_2CF_2$—;

(v) Rf—$(O$—$CF_2CF_2)_n$—O—$CF_2$-T, with n=1, 2, 3, 4 or 5, and Rf being a linear or branched per- or partly fluorinated alkyl chain, wherein the alkyl chain can be interrupted by O atoms;

(vi) an oligomeric compound obtainable by the polymerization or copolymerization of monomers selected from the group consisting of vinylidenfluoride, hexafluoropropylenoxide, tetrafluoroethylene, 2,2,3,3-tetrafluorooxetane, trifluoroethylene and monofluoroethylene, wherein at least one chain-end of the oligomeric compound is represented by function T;

(vii) and mixtures thereof, wherein T, T1, and T2 can be equal or different and are independently selected from —COOR, —CONR$^b$R$^c$, —CH$_2$OH, —CF$_2$OR, —CHFOH, —CHFOR, —CH$_2$OR or —F, with R being a linear or branched alkyl chain of C1 to C9, aryl group of C1 to C9, and alkylaryl group of C1 to C9, each of which may optionally be substituted with one or more substituents selected from the group consisting of hydroxyl, amino group, halogen atom, an SiH group, and a group capable of reacting with SiH, R$^b$ and R$^c$ independently represent H or have a meaning as given for R.

2. A curable dental composition according to claim 1 wherein said component (A) is a curable polysiloxane polymer, the polymer containing at least two functional groups capable of reacting with a SiH group in the presence of a hydrosilation catalyst; component (B) is a crosslinker compound containing at least two SiH groups and component (C) is a catalyst capable of catalyzing a hydrosilation reaction.

3. The dental composition according to claim 1, fulfilling at least one of the following parameters:
consistency (according to ISO 4823): 0, 1, 2 or 3,
setting time: within about 15 min after mixing at ambient conditions.

4. The dental composition according to claim 1, characterized after hardening by at least one of the following parameters:
tensile strength (according to DIN 53504): at least about 0.2 MPa,
elongation at break (according to DIN 53504): at least about 30%,
recovery from deformation (according to DIN 53504): at least about 90%,
Shore A hardness (according to DIN 53 505; 24 h) at least about 20.

5. The dental composition of claim 1 containing the F-containing compound in an amount effective to provide a composition having a water contact angle of less than about 20° at a water drop age of 10 s ($\Theta_{10s}$), no later than 60 s after mixing of the components and/or having an initial water contact angle of less than about 80° ($\Theta_{0s}$), no later than 40 s after mixing of the components.

6. The dental composition of claim 1, wherein the F-containing compound is selected from
Rf—O—CHF-T, with Rf being a linear or branched per- or partly fluorinated alkyl chain (C1 to C6), which can be interrupted by one or more oxygen atoms,
Rf—O—$CF_2$-T, with Rf being a linear or branched per- or partly fluorinated alkyl chain (C1 to C6), which can be interrupted by one or more oxygen atoms, Rf—O—CHF—CF$_2$-T, with Rf being a linear or branched per- or partly fluorinated alkyl chain (C1 to C6), which can be interrupted by one or more oxygen atoms, Rf—O—CF$_2$—CF$_2$-T, with Rf being a linear or branched per- or partly fluorinated alkyl chain (C1 to C6), which can be interrupted by one or more oxygen atoms, Rf—O—CF$_2$—CHF-T, with Rf being a linear or branched per- or partly fluorinated alkyl chain (C1 to C6), which can be interrupted by one or more oxygen atoms, Rf—O—CF$_2$—CHF—CF$_2$-T, with Rf being a linear or branched per- or partly fluorinated alkyl chain (C1 to C6), which can be interrupted by one or more oxygen atoms, Rf—(O—CF$_2$)$_u$—O—CF$_2$-T, with Rf being a linear or branched per- or partly fluorinated alkyl chain (C1 to C6), which can be interrupted by one or more oxygen atoms, and u=1, 2, 3, 4, 5 or 6, Rf—(O—CF$_2$—CF$_2$)$_k$—O—CF$_2$-T, with Rf being a linear or branched per- or partly fluorinated alkyl chain (C1 to C6), which can be interrupted by one or more oxygen atoms, and k=1, 2, 3, 4 or 5, Rf—(O—CF$_2$—CF$_2$—CF$_2$)$_n$—O—CF$_2$—CF$_2$-T, with n=1 to 25 and Rf being a linear or branched per- or partly fluorinated alkyl chain (C1 to C6), wherein the alkyl chain can be interrupted by O atoms, T-CF$_2$—O—(CF$_2$—CF$_2$—O)$_p$—(CF$_2$—O)$_q$—CF$_2$-T, with p/q=0.5 to 3.0 and an molecular weigth in the range of about 500 to about 4000 g/mol, T-CF$_2$—(O—CF(CF$_3$)—CF$_2$)$_n$—(O—CF$_2$)$_m$—O—CF$_2$-T, with n/m=20-40 and a molecular weight in the range of about 650 to about 3200 g/mol, CF$_3$—(CF$_2$)$_2$—(OCF(CF$_3$)—CF$_2$)$_z$—O—CF(CF$_3$)-T, with z=0, 1, 2, 3, 4, 5, 6, 7 or 8, CF$_3$—CHF—O—(CF$_2$)$_o$-T, with o=1, 2, 3, 4, 5 or 6, CF$_3$—CF$_2$—O—(CF$_2$)$_o$-T, with o=1, 2, 3, 4, 5 or 6, and mixtures thereof, T having the meaning as defined for T$^1$ and T$^2$ in claim 15.

7. The dental composition of claim 1, wherein the F-containing compound is selected from CF$_3$—O—CF$_2$—O—CF$_2$—CF$_2$—O—CHF-T
CF$_3$—(O—CF$_2$)$_2$—O—CF$_2$—CF$_2$—O—CHF-T
CF$_3$—(O—CF$_2$)$_3$—O—CF$_2$—CF$_2$—O—CHF-T
CF$_3$—O—CF$_2$—O—CF$_2$—CF$_2$—O—CHF—CF$_2$-T
CF$_3$—(O—CF$_2$)$_2$—O—CF$_2$—CF$_2$—O—CHF—CF$_2$-T
CF$_3$—(O—CF$_2$)$_3$—O—CF$_2$—CF$_2$—O—CHF—CF$_2$-T
C$_3$F$_7$—O—CF$_2$—CHF-T
CF$_3$—O—CF$_2$—O—CF$_2$—CF$_2$—O—CF$_2$—CHF-T
CF$_3$(O—CF$_2$)$_2$—O—CF$_2$—CF$_2$—O—CF$_2$—CHF-T
CF$_3$—(O—CF$_2$)$_3$—O—CF$_2$—CF$_2$—O—CF$_2$—CHF-T
C$_3$F$_7$—O—CF$_2$—CHF—CF$_2$-T
CF$_3$—O—CF$_2$—CF$_2$—CF$_2$—O—CF$_2$—CHF—CF$_2$-T
CF$_3$—O—CF$_2$—O—CF$_2$—CF$_2$—O—CF$_2$—CHF—CF$_2$-T
CF$_3$—(O—CF$_2$)$_2$—O—CF$_2$—CF$_2$—O—CF$_2$—CHF—CF$_2$-T
CF$_3$—(O—CF$_2$)$_3$—O—CF$_2$—CF$_2$—O—CF$_2$—CHF—CF$_2$-T
CF$_3$—(O—CF$_2$)$_3$—O—CF$_2$-T
CF$_3$—(O—CF$_2$)$_5$—O—CF$_2$-T
C$_2$F$_5$—(O—CF$_2$—CF$_2$)$_1$—O—CF$_2$-T
C$_3$F$_7$—(O—CF$_2$—CF$_2$)$_1$—O—CF$_2$-T
C$_4$F$_9$—(O—CF$_2$—CF$_2$)$_1$—O—CF$_2$-T
C$_2$F$_5$—(O—CF$_2$—CF$_2$)$_2$—O—CF$_2$-T
CF$_3$—(O—CF$_2$—CF$_2$)$_2$—O—CF$_2$-T
C$_3$F$_7$—(O—CF$_2$—CF$_2$)$_2$—O—CF$_2$-T
C$_4$F$_9$—(O—CF$_2$—CF$_2$)$_2$—O—CF$_2$-T
CF$_3$—(CF$_2$)$_2$—(O—CF(CF$_3$)—CF$_2$)$_2$—O—CF(CF$_3$)-T
CF$_3$—(CF$_2$)$_2$—(O—CF(CF$_3$)—CF$_2$)$_3$—O—CF(CF$_3$)-T
CF$_3$—(CF$_2$)$_2$—(O—CF(CF$_3$)—CF$_2$)$_4$—O—CF(CF$_3$)-T
CF$_3$—(CF$_2$)2-(O—CF(CF$_3$)—CF$_2$)$_5$—O—CF(CF$_3$)-T
CF$_3$—(CF$_2$)$_2$—(O—CF(CF$_3$)—CF$_2$)$_6$—O—CF(CF$_3$)-T
CF$_3$—CFH—O—(CF$_2$)$_3$-T
CF$_3$—CFH—O—(CF$_2$)$_5$-T
CF$_3$—CF$_2$—O—(CF$_2$)$_3$-T
CF$_3$—CF$_2$—O—(CF$_2$)$_5$-T
Rf—(O—CF$_2$—CF$_2$—CF$_2$)$_n$—O—CF$_2$—CF$_2$-T with n=1 to 25 and Rf being a linear or branched per- or partly fluorinated alkyl rest (C1 to C6), wherein the alkyl chain can be interrupted by O atoms, T-CF$_2$—O—(CF$_2$—CF$_2$—O)$_p$—(CF$_2$—O)$_q$—CF$_2$-T, with p/q=0.5 to 3.0 and a molecular weight in the range of about 500 to about 4000 g/mol, T-CF$_2$—(O—CF(CF$_3$)—CF$_2$)$_n$—(O—CF$_2$)$_m$—O—CF$_2$-T with n/m=about 20 to 40 and a molecular weight in the range of about 650 to about 3200 g/mol, and mixtures thereof, T having the meaning as defined for T$^1$ and T$^2$ in claim 1.

8. The dental composition of claim 1, wherein the molar ratio of F-containing compound to surfactant is in a range of 0.1 to about 4.

9. The dental composition of claim 1 comprising at least one of the following components:
f) filler as component (F),
g) at least one polydimethylsiloxane without aliphatically unsaturated groups as component (G),
h) additives as component (H) selected from retarders, rheology modifiers, inhibitors, pigments, plasticizers, dyes, pigments, odorous substances, flavourings, stabilizers, hydrogen scavenger alone or in admixture.

10. The dental composition of claim 9, wherein the components are present in the following amounts:
component (A): from about 20 wt.-% to about 80 wt.-%,
component (B): from about 0.1 wt.-% to about 15 wt.-%,
component (C): from about 0.001 wt.-% to about 0.1 wt.-%,
component (D): from about 0.1 wt.-% to about 5 wt.-%,
component (E): from about 0.1 wt.-% to about 5 wt.-%,
component (F): from about 0 wt.-% to about 75 wt.-%,
component (G): from about 0 wt.-% to about 10 wt.-%,
component (H): from about 0 wt.-% to about 10 wt.-%,
wt.-% with respect to the whole composition.

11. A kit of parts comprising a base paste and a catalyst paste separated from each other before use, comprising the curable dental composition of claim 1 wherein the base paste comprises components (A) and (B) and the catalyst paste comprises component (C) or (C) and (A) and wherein component (D) and/or (E) and the other optional components (F), (G) and (H) can be present either in the base paste or the catalyst paste or the base paste and the catalyst paste, wherein components (A) to (H) are as described in any of the preceding claims.

12. The kit of parts according to claim 11, wherein component (D) is present in the base paste and component (E) is present in the catalyst paste.

13. A method of producing a dental composition comprising the step of combining the F-containing compound with a hardenable matrix comprising a surfactant, wherein the surfactant and the F-containing compound are as described in claim 1.

14. The dental composition as described in claim 1, wherein the dental composition is used for the preparation of and/or as an impression material or for the preparation of and/or crowns and bridges.

15. The F-containing component as described in claim 1, wherein the F-containing component is used for enhancing the wettability of a hardenable composition.

* * * * *

UNITED STATES PATENT AND TRADEMARK OFFICE
CERTIFICATE OF CORRECTION

| | |
|---|---|
| PATENT NO. | : 8,466,210 B2 |
| APPLICATION NO. | : 12/747927 |
| DATED | : June 18, 2013 |
| INVENTOR(S) | : Joachim Zech |

It is certified that error appears in the above-identified patent and that said Letters Patent is hereby corrected as shown below:

Title Page
Column 2 item (56), (Other Publications); Line 2, Delete "Angels" and insert -- Angles --, therefor.

Title Page 2
Column 1 item (56), (U.S. Patent Documents); Line 21, Delete "2,337,024" and insert -- 5,964,743 --, therefor.

In the Specifications:

Column 4
Line 21; Delete "Rb and Rc" and insert -- $R^b$ and $R^c$ --, therefor.

Column 7
Line 43-44; Delete "Silwett™" and insert -- Silwet™ --, therefor.

Column 12
Line 66; Delete "silic" and insert -- silicic --, therefor.
Line 67; Delete "polysilic" and insert -- polysilicic --, therefor.

Column 16
Line 1-10; Delete "Such................Pluronic." and insert the same on Col. 15, Line 67, after "well." as a continuation of the same paragraph.

Column 17
Line 53; Delete "atoms" and insert -- atoms. --, therefor.

Column 18
Line 1; Delete "vinylidenfluoride," and insert -- vinylidenefluoride, --, therefor.
Line 9; Delete "vinylidenfluoride," and insert -- vinylidenefluoride, --, therefor.

Signed and Sealed this
Twenty-eighth Day of January, 2014

Michelle K. Lee
*Deputy Director of the United States Patent and Trademark Office*

CERTIFICATE OF CORRECTION (continued)
U.S. Pat. No. 8,466,210 B2

Column 20
Line 45; Delete "silicone" and insert -- silicon --, therefor.
Line 46; Delete "silicone" and insert -- silicon --, therefor.
Line 47-48; Delete "silicone" and insert -- silicon --, therefor.

Column 21
Line 65-66; Delete "plastizers" and insert -- plasticizers --, therefor.

Column 22
Line 19; Delete "an" and insert -- on --, therefor.
Line 64; Delete "I:" and insert -- (I): --, therefor.

Column 25
Line 46; Delete "steps." and insert -- steps). --, therefor.

Column 27-28
Line 1 (Table 1); Delete "catalyste" and insert -- catalyst --, therefor.
Line 20 (Approx.) (Row 4) (Table 1); Insert -- Catalyst paste B --. (As a heading)
Line 4 (Below Table 1); Delete "LCC" and insert -- LCC. --, therefor.
Line 9 (Below Table 1); Delete "perfluoroalcanol" and insert -- perfluoroalkanol --, therefor.

Column 29
Line 14; Delete "$(\theta=10°)$" and insert -- ($\theta$=10°) --, therefor.

Column 35
Line 2; Delete "ethyoxylate;" and insert -- ethoxylate; --, therefor.

In the Claims:

Column 37
Line 64; Claim 1, delete "$(OcF_2)_m$" and insert -- "$(OCF_2)_m$ --, therefor.

Column 38
Line 11-12; Claim 1, delete "vinylidenfluoride," and insert vinylidenefluoride, --, therefor.

Column 39
Line 26; Claim 6, delete "weigth" and insert -- weight --, therefor.
Line 35; Claim 6, delete "15." and insert -- 1. --, therefor.
Line 48; Claim 7, delete "$CF_9$" and insert -- $CF_2$ --, therefor.

Column 40
Line 1; Claim 7, delete "$(CF_2)2$" and insert -- $(CF_2)_2$ --, therefor.
Line 28; Claim 9, delete "plastizers," and insert -- plasticizers, --, therefor.